United States Patent
Iguchi et al.

(10) Patent No.: US 10,386,231 B2
(45) Date of Patent: Aug. 20, 2019

(54) CARBON ISOTOPE ANALYSIS DEVICE AND CARBON ISOTOPE ANALYSIS METHOD

(71) Applicants: NATIONAL UNIVERSITY CORPORATION NAGOYA UNIVERSITY, Nagoya-shi, Aichi (JP); SEKISUI MEDICAL CO., LTD., Tokyo (JP)

(72) Inventors: Tetsuo Iguchi, Nagoya (JP); Hideki Tomita, Nagoya (JP); Norihiko Nishizawa, Nagoya (JP); Takahiro Hirotsu, Nagoya (JP); Satoshi Yuruzume, Nagoya (JP); Ryohei Terabayashi, Nagoya (JP); Toshinari Oh-Hara, Tokyo (JP); Akira Ideno, Tokyo (JP); Atsushi Sato, Tokyo (JP)

(73) Assignees: NATIONAL UNIVERSITY CORPORATION NAGOYA UNIVERSITY, Nagoya-Shi (JP); SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 15/555,219

(22) PCT Filed: Mar. 2, 2016

(86) PCT No.: PCT/JP2016/056390
§ 371 (c)(1),
(2) Date: Sep. 1, 2017

(87) PCT Pub. No.: WO2016/140254
PCT Pub. Date: Sep. 9, 2016

(65) Prior Publication Data
US 2018/0052047 A1 Feb. 22, 2018

(30) Foreign Application Priority Data
Mar. 4, 2015 (JP) .................. 2015-042749

(51) Int. Cl.
*G01J 1/12* (2006.01)
*G01J 3/02* (2006.01)
(Continued)

(52) U.S. Cl.
CPC ............. *G01J 3/0218* (2013.01); *G01J 1/124* (2013.01); *G01J 3/0208* (2013.01); *G01J 3/42* (2013.01);
(Continued)

(58) Field of Classification Search
CPC .............. G01N 21/39; G01N 21/3504; G01N 2201/06113; G01N 33/0004;
(Continued)

(56) References Cited

U.S. PATENT DOCUMENTS 5,012,052 A * 4/1991 Hayes ................ G01N 30/7206
250/282
6,618,531 B1 9/2003 Goto et al.
(Continued)

FOREIGN PATENT DOCUMENTS

EP 3106859 A1 12/2016
JP 3390755 B2 3/2003
(Continued)

OTHER PUBLICATIONS

Keilmann et al., "Mid-infrared Frequency Comb Spanning an Octave Based on an Er Fiber Laser and Difference-Frequency Generation," J Infrared Milli Terahz Waves, vol. 33, 2012 (Published online Apr. 17, 2012), pp. 479-484, XP035048375.
(Continued)

*Primary Examiner* — David P Porta
*Assistant Examiner* — Meenakshi S Sahu
(74) *Attorney, Agent, or Firm* — Birch, Stewart, Kolasch & Birch, LLP

(57) ABSTRACT

A carbon isotope analyzer 1 includes a carbon dioxide isotope generator 40 that includes a combustion unit that
(Continued)

generates gas containing carbon dioxide isotope from carbon isotope, and a carbon dioxide isotope purifying unit; a spectrometer 10 including an optical resonator 11 having a pair of mirrors 12, and a photodetector 15 that determines the intensity of light transmitted from the optical resonator 11; and a light generator 20 including a light source 23, a first optical fiber 21 to transmit a light beam from the light source 23, a second optical fiber 22 for wavelength conversion, the second optical fiber 22 splitting from the first optical fiber 21 at a point and combining with the first optical fiber 21 at another point downstream of the splitting point, and a non-linear optical crystal 25 that generates light having the absorption wavelength of the carbon dioxide isotope on the basis of the difference in frequency between light beams transmitted through the optical crystal 25. The carbon isotope analyzer 1 is a simple and convenient apparatus that can analyze isotope $^{14}C$.

19 Claims, 25 Drawing Sheets

(51) Int. Cl.
| | | |
|---|---|---|
| *G01N 21/3504* | (2014.01) | |
| *G01N 21/01* | (2006.01) | |
| *G02F 1/37* | (2006.01) | |
| *G01J 3/42* | (2006.01) | |
| *G01N 30/88* | (2006.01) | |
| *G02F 1/355* | (2006.01) | |

(52) U.S. Cl.
CPC .......... *G01N 21/01* (2013.01); *G01N 21/3504* (2013.01); *G01N 30/88* (2013.01); *G02F 1/3551* (2013.01); *G02F 1/37* (2013.01); *G01N 2030/8868* (2013.01); *G01N 2201/06113* (2013.01); *G01N 2201/08* (2013.01); *G02F 2201/02* (2013.01); *G02F 2203/56* (2013.01)

(58) Field of Classification Search
CPC ..... G01N 2021/0346; G01N 2021/399; G01N 2021/8578; G01N 21/031; G01N 33/0006; G01N 33/497; G01N 2021/1704; G01N 2201/08; G02F 1/3532
USPC ...................................................... 250/338.1
See application file for complete search history.

(56) References Cited

U.S. PATENT DOCUMENTS

| | | | | |
|---|---|---|---|---|
| 2003/0146760 | A1* | 8/2003 | Kogawa | G01T 1/24 324/464 |
| 2004/0235000 | A1 | 11/2004 | Spalding et al. | |
| 2007/0018091 | A1* | 1/2007 | Garner | B01D 59/44 250/283 |
| 2007/0074541 | A1* | 4/2007 | Badding | C03B 19/106 65/413 |
| 2009/0233371 | A1 | 9/2009 | Tashiro | |
| 2011/0302992 | A1* | 12/2011 | Robbins | A61B 5/083 73/23.3 |
| 2012/0162748 | A1 | 6/2012 | Fermann et al. | |
| 2012/0241622 | A1 | 9/2012 | Heyne et al. | |
| 2012/0287418 | A1* | 11/2012 | Scherer | G01N 21/61 356/51 |
| 2014/0219296 | A1 | 8/2014 | Fermann et al. | |
| 2016/0011101 | A1 | 1/2016 | Ognibene et al. | |
| 2016/0054180 | A1* | 2/2016 | Giusfredi | G01J 3/42 250/339.07 |
| 2016/0349177 | A1 | 12/2016 | Iguchi et al. | |

FOREIGN PATENT DOCUMENTS

| | | |
|---|---|---|
| JP | 2004-287074 A | 10/2004 |
| JP | 2005-537490 A | 12/2005 |
| JP | 2007-85874 A | 4/2007 |
| JP | 2014-504380 A | 2/2014 |
| JP | 6004412 B2 | 10/2016 |

OTHER PUBLICATIONS

McCartt, "Development of a Low-temperature Cavity Ring-down Spectrometer for the Detection of Carbon-14," Stanford University, Department of Mechanical Engineering, Doctoral Thesis, Jul. 2014, pp. 1-149 (175 pages total), XP55506419.
Partial Supplementary European Search Report, dated Sep. 25, 2018, for European Application No. 16758947.2.
English translation of the International Preliminary Report on Patentability (Forms PCT/IB/338 and PCT/IPEA/409), dated Sep. 8, 2017, for International Application No. PCT/JP2016/056390.
English translation of the International Preliminary Report on Patentability (Form PCT/IPEA/409) for International Application No. PCT/JP2016/056390, dated Aug. 1, 2017.
Galli et al., "Molecular Gas Sensing Below Parts Per Trillion: Radiocarbon-Dioxide Optical Detection," Physical Review Letters, vol. 107, Dec. 30, 2011, pp. 270802-1-270802-4.
International Search Report (Form PCT/ISA/210) for International Application No. PCT/JP2016/056390, dated May 24, 2016.
Ishizawa et al., "Demonstration of Carrier Envelope Offset Locking with Low Pulse Energy," Optics Express, vol. 16, No. 7, Mar. 31, 2008 (published online Mar. 21, 2008), pp. 4706-4712.
Shigematsu, "Liquid Scintillation Counting Technique (VI) Application in Biological Researches," Radioisotopes, vol. 24, No. 6, Jun. 1975, pp. 443-453.
Erny et al., "Mid-infrared difference-frequency generation of ultrashort pulses tunable between 3.2 and 4.8 μm from a compact fiber source", Optics Letters, vol. 32, No. 9, May 1, 2007, XP001541009, pp. 1138-1140 (3 pages).
Extended European Search Report, dated Jan. 24, 2019, for corresponding European Application No. 16758947.2.
Ingalls et al., "Radiocarbon dating of diatom-bound organic compounds", Marine Chemistry, vol. 92, 2004 (available online Oct. 1, 2004), pp. 91-105 (15 pages).
King et al., "Supercritical Fluid Extraction (SFE) for the Removal of Lipid and Interfering Compounds Prior to Radiocarbon Dating of Archaeological Artifacts Using Teledyne Isco Syringe Pumps", Syringe Pump Application Note AN30, Jan. 9, 2012, 5 pages.
Lindauer et al., "Carbonate Sample Preparation for $^{14}C$ Dating Using an Elemental Analyzer", Radiocarbon, vol. 55, No. 2-3, 2013, pp. 364-372 (9 pages).
Nakamura et al., "Offset-free broadband Yb:fiber optical frequency comb for optical clocks", Optics Express, vol. 23, No. 15, Jul. 27, 2015, pp. 19376-19381 (6 pages).
Ruehl et al., "Widely-tunable mid-infrared frequency comb source based on difference frequency generation", Optics Letters, vol. 37, No. 12, Jun. 15, 2012 (published online Jun. 6, 2012), XP001576257, pp. 2232-2234 (3 pages).
Zimmermann et al., "Optical clockwork with an offset-free difference-frequency comb: accuracy of sum- and difference-frequency generation", Optics Letters, vol. 29, No. 3, Feb. 1, 2004, XP002336000, pp. 310-312 (3 pages).

\* cited by examiner

51: OPTICAL RESONATOR
52: HIGHLY REFLECTIVE MIRROR
53: RING PIEZOELECTRIC ACTUATOR
54: WATER-COOLING HEATSINK
55: MIRROR DRIVING MECHANISM
56: GAS CELL FOR ANALYSIS
58: ADIABATIC CHAMBER
59: PELTIER ELEMENT

Result 2

|        | Regression equation | Relative slope (%) |
|--------|---------------------|--------------------|
| Solid  | y = 29647x + 20.2   | 100                |
| 10 µL  | y = 29455x + 188    | 99.4               |
| 20 µL  | y = 28679x + 408    | 96.7               |
| 50 µL  | y = 28481x + 586    | 96.1               |

CARBON ISOTOPE ANALYSIS DEVICE AND CARBON ISOTOPE ANALYSIS METHOD

TECHNICAL FIELD

The present invention relates to a carbon isotope analyzer and a method of analyzing carbon isotope. In specific, the present invention relates to a radioactive carbon isotope analyzer useful for analysis of radioactive carbon $^{14}C$ and a method of analyzing the radioactive carbon isotope.

BACKGROUND ART

Carbon isotope analysis has been applied to a variety of fields, including assessment of environmental dynamics based on the carbon cycle, and historical and empirical research through radiocarbon dating. The natural abundances of carbon isotope, which may vary with regional or environmental factors, are as follows: 98.89% for $^{12}C$ (stable isotope), 1.11% for $^{13}C$ (stable isotope), and $1\times10^{-10}$% for $^{14}C$ (radioisotope). These isotopes, which have different masses, exhibit the same chemical behavior. Thus, artificial enrichment of an isotope of low abundance and accurate analysis of the isotope can be applied to observation of a variety of reactions.

In the clinical field, in vivo administration and analysis of a compound labeled with, for example, radioactive carbon $^{14}C$ are very useful for assessment of drug disposition. For example, such a labeled compound is used for practical analysis in Phase I or Phase IIa of the drug development process. Administration of a compound labeled with radioactive carbon $^{14}C$ (hereinafter may be referred to simply as "$^{14}C$") to a human body at a very small dose (hereinafter may be referred to as "microdose") (i.e., less than the pharmacologically active dose of the compound) and analysis of the labeled compound are expected to significantly reduce the lead time for a drug discovery process because the analysis provides findings on drug efficacy and toxicity caused by drug disposition.

Examples of the traditional $^{14}C$ analysis include liquid scintillation counting (hereinafter may be referred to as "LSC") and accelerator mass spectrometry (hereinafter may be referred to as "AMS").

LSC involves the use of a relatively small table-top analyzer and thus enables convenient and rapid analysis. Unfortunately, LSC cannot be used in clinical trials because of its low $^{14}C$ detection sensitivity (10 dpm/mL). In contrast, AMS can be used in clinical trials because of its high NC detection sensitivity (0.001 dpm/mL), which is less than one thousandth of that of LSC. Unfortunately, the use of AMS is restricted because AMS requires a large and expensive analyzer. Since only around fifteens of AMS analyzers are provided in Japan, analysis of one sample requires about one week due to a long waiting time for samples to be analyzed. Thus, a demand has arisen for development of a convenient and rapid method of analyzing $^{14}C$.

RELATED ART

Patent Document 1: Japanese Patent No. 3390755

Non-Patent Document

Non-Patent Document 1: I. Galli, et al., Phy. Rev. Lett. 2011, 107, 270802

SUMMARY OF INVENTION

Several techniques have been proposed for solving the problems (see Non-Patent Document 1 and Patent Document 1, for example).

I. Galli, et al. reported the analysis of $^{14}C$ of a natural abundance level by cavity ring-down spectroscopy (hereinafter may be referred to as "CRDS") in Non-Patent Document 1, and this analysis has received attention.

Unfortunately, the $^{14}C$ analysis by CRDS involves the use of a 4.5-μm laser source having a very intricate structure. Thus, a demand has arisen for a simple and convenient apparatus or method for analyzing $^{14}C$.

An object of the present invention is to provide a simple and convenient apparatus that can analyze the carbon isotope $^{14}C$ and a method of analyzing the carbon isotopes.

Solution to Problem

The present invention provides the following aspects:

Aspect <1> A carbon isotope analyzer including a carbon dioxide isotope generator provided with a combustion unit that generates gas containing carbon dioxide isotope from carbon isotope and a carbon dioxide isotope purifying unit; a spectrometer including an optical resonator having a pair of mirrors and a photodetector that determines the intensity of light transmitted from the optical resonator; and a light generator including a light source, a first optical fiber to transmit a light beam from the light source, a second optical fiber for wavelength conversion, the second optical fiber splitting from the first optical fiber at a splitting node and coupling with the first optical fiber at a coupling node downstream of the splitting node, and a nonlinear optical crystal that generates light at the absorption wavelength of the carbon dioxide isotope depending on the difference in frequency between light beams transmitted through the optical crystal.

Aspect <2> The carbon isotope analyzer of Aspect <1>, wherein the dioxide isotope purifying unit includes at least one of a gaseous contaminant separator and a carbon dioxide isotope enricher.

Aspect <3> The carbon isotope analyzer according to Aspect <1> or <2>, wherein the carbon isotope is radioactive carbon $^{14}C$, and the carbon dioxide isotope is radioactive carbon dioxide $^{14}CO_2$.

Aspect <4> The carbon isotope analyzer of any one of Aspects <1> to <3>, wherein the light source generates frequency comb light.

Aspect <5> The light source of any one of Aspects <1> to <4>, the light source includes a fiber laser.

Aspect <6> The carbon isotope analyzer of any one of Aspects <1> to <5>, wherein the light is at the absorption wavelength of the carbon dioxide isotope is light of a 4.5-μm wavelength range.

Aspect <7> The carbon isotope analyzer of any one of Aspects <1> to <6>, wherein the carbon dioxide isotope generator comprises a total organic carbon gas generator that generates the carbon dioxide isotope.

Aspect <8> The carbon isotope analyzer carbon isotope analyzer of any one of Aspects <1> to <7>, wherein the first optical fiber extends from the light source to the optical resonator.

Aspect <9> The carbon isotope analyzer of any one of Aspects <1> to <8>, wherein the first optical fiber includes a fiber component (a) extending from the light source to the nonlinear optical crystal, and a mid-infrared fiber component (b) extending from the non-linear optical crystal to the optical resonator.

Aspect <10> The carbon isotope analyzer of any one of Aspects <1> to <7> and <9>, the light generator further includes an optical transmitter that transmits light from the nonlinear optical crystal to the optical resonator.

Aspect <11> The carbon isotope analyzer of Aspect <10>, wherein the first optical fiber is the fiber component (a) extending from the light source to the non-linear optical crystal.

Aspect <12> The carbon isotope analyzer of any one of Aspects <1> to <7> and <9> to <11>, wherein the light generator further includes an optical lens between a coupling node between the first and the second optical fibers and the non-linear optical crystal and/or another optical lens between the non-linear optical crystal and the optical resonator.

Aspect <13> The carbon isotope analyzer of any one of Aspects <1> to <12>, wherein the first optical fiber has a downstream end abutting on one of the mirrors.

Aspect <14> The carbon isotope analyzer of any one of Aspects <1> to <13>, wherein the second optical fiber includes a nonlinear optical fiber.

Aspect <15> The carbon isotope analyzer of any one of Aspects <1> to <14>, the spectrometer further includes a cooler that cools the optical resonator.

Aspect <16> The carbon isotope analyzer of any one of Aspects <1> to <15>, wherein the spectrometer further includes a vacuum device that accommodates the optical resonator.

Aspect <17> The carbon isotope analyzer of any one of Aspects <1> to <16>, wherein the spectrometer further includes a vibration dampener.

Aspect <18> The carbon isotope analyzer of any one of Aspects <1> to <17>, wherein the spectrometer further includes a diffraction grating that disperses the transmitted light, and the photodetector includes a first sub-detector and a second sub-detector that detect transmitted light beams having different wavelengths.

Aspect <19> The carbon isotope analyzer of any one of Aspects <1> to <18>, wherein the nonlinear optical crystal is selected from a PPMGSLT crystal, PPLN crystal, and GaSe crystal.

Aspect <20> The carbon isotope analyzer of any one of Aspects <1> to <19>, wherein the analyzer has a detection sensitivity of about 0.1 dpm/ml to a radioactive carbon isotope $^{14}C$.

Aspect <21> A carbon isotope analyzer including a carbon dioxide isotope generator including a combustion unit that generates gas containing carbon dioxide isotope from carbon isotope, and a carbon dioxide isotope purifying unit; a spectrometer including an optical resonator having a pair of mirrors, and a photodetector that determines the intensity of light transmitted from the optical resonator; and a light generator including a single light source, an optical fiber that transmits the light from the light source and spreads the spectrum of the light, and a nonlinear optical crystal that generates light at the absorption wavelength of the carbon dioxide isotope on the basis of the difference in frequency between light beams transmitted through the optical crystal.

Aspect <22> The carbon isotope analyzer of Aspect <21>, further including a wavelength filter that separates the light from the light source into a plurality of spectral components with a wavelength filter, adjusts the relative time delays of the spectral components, respectively, and focuses the spectral components on a nonlinear crystal.

Aspect <23> The carbon isotope analyzer of Aspect <21>, further including a delay line that separates the light from the light source into a plurality of spectral components with a wavelength filter, adjust the relative time delays of the spectral components, respectively, and focuses the spectral components on a nonlinear crystal.

Aspect <24> A light generator including: a light source; an optical fiber that transmits light from the light source and spreads the spectrum of the light; a wavelength filter that separates the light from the optical fiber into a plurality of spectral components with a wavelength filter, adjusts the time lags of the spectral components, respectively, and focuses the spectral components on a nonlinear crystal; and a nonlinear optical crystal that generates light at the absorption wavelength of the carbon dioxide isotope depending on the difference in frequency between light beams transmitted through the optical crystal.

Aspect <25> The light generator of Aspect <24>, wherein the wavelength filter including a delay line that separates the light from the light source into a plurality of spectral components with a wavelength filter.

Aspect <26> A method of analyzing carbon isotope, involving, the steps of: generating carbon dioxide isotope from carbon isotope; feeding the carbon dioxide isotope into an optical resonator having a pair of mirrors; generating a plurality of light beams having different wavelengths from a single light source, transmitting the light beams through a non-linear optical crystal, and thereby generating irradiation light at the absorption wavelength of the carbon dioxide isotope from differences between the frequencies; measuring the intensity of the transmitted light generated by resonance of carbon dioxide isotope excited by the irradiation light; and calculating the concentration of the carbon isotope from the intensity of the transmitted light.

Aspect <27> The method of analyzing carbon dioxide isotope of Aspect <26>, further involving the steps of, before the step of generating carbon dioxide isotope: removing a biological carbon source from a biological substance containing carbon isotope with an organic solvent; and removing a carbon source derived from the organic solvent from the resulting sample.

Aspect <28> The method of analyzing carbon dioxide isotope of Aspect <26>, wherein the step of generating carbon dioxide isotope involves removing a gaseous contaminant and/or separating the carbon dioxide isotope from the gaseous contaminant.

Aspect <29> The method of analyzing carbon isotope of Aspect <26>, wherein the carbon isotope is the radioactive carbon isotope $^{14}C$, and the carbon dioxide isotope is the radioactive carbon dioxide isotope $^{14}CO_2$.

Effects of Invention

The present invention provides an apparatus and a method of analyzing carbon isotope $^{14}C$ in a simple and convenient manner.

DESCRIPTION OF EMBODIMENTS

Figure 1:
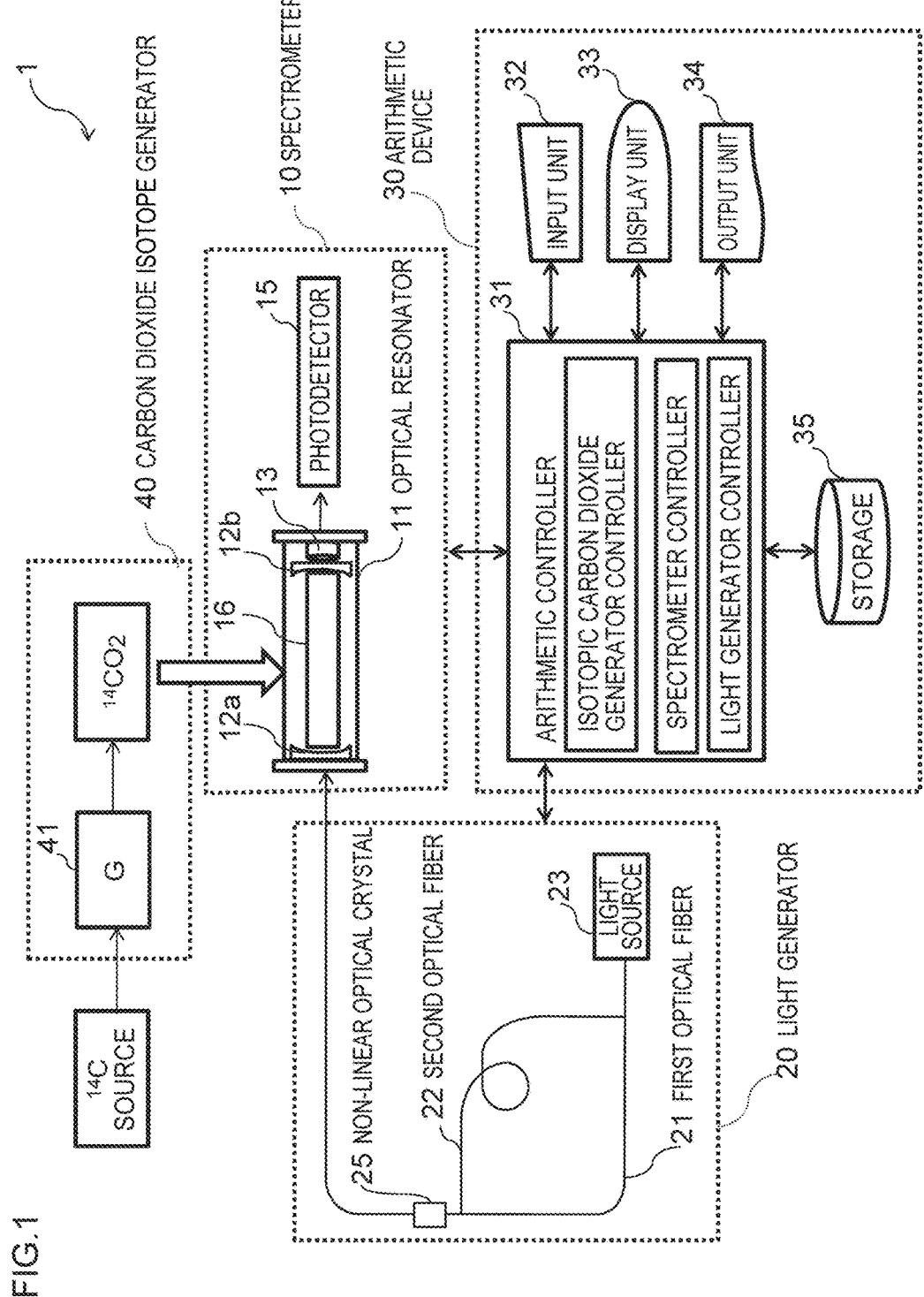
FIG. 1 is a conceptual view of a carbon isotope analyzer.

The present invention relates to a carbon isotope analyzer including a carbon dioxide isotope generator including a combustion unit that generates gas containing carbon dioxide isotope from carbon isotope and a carbon dioxide isotope purifying unit; a spectrometer including an optical resonator having a pair of mirrors and a photodetector that determines the intensity of light transmitted from the optical resonator; and a light generator including a single light source, an optical path that generates a plurality of light beams with different frequencies from the light generated at the light source, and a nonlinear optical crystal that generates light having an absorption wavelength of the carbon dioxide isotope on the basis of the difference in frequency between light beams transmitted through the optical crystal.

The optical path includes, for example, a first optical fiber transmitting the light from the light source, and second optical fiber for wavelength conversion splitting from the first optical fiber at a splitting node and coupling with the first optical fiber at a coupling node downstream of the splitting node. Alternatively, the optical path includes an optical fiber that transmits the light from the light source and spreads the spectrum of the light, a wavelength filter that separates the light from the light source into a plurality of spectral components, and focuses a predetermined spectrum component on a nonlinear crystal.

The present invention will now be described by way of embodiments, which should not be construed to limit the present invention. In the drawings, the same or similar reference signs are assigned to components having the same or similar functions without redundant description. It should be noted that the drawings are schematic and thus the actual dimensions of each component should be determined in view of the following description. It should be understood that the relative dimensions and ratios between the drawings may be different from each other.

(Carbon Isotope Analyzer)

FIG. 1 is a conceptual view of the carbon isotope analyzer. The carbon isotope analyzer 1 includes a carbon dioxide isotope generator 40, a light generator 20, a spectrometer 10, and an arithmetic device 30. In this embodiment, a radioactive isotope $^{14}C$, carbon isotope will be exemplified as an analytical sample. The absorption wavelength range of the carbon dioxide isotope $^{14}CO_2$ generated from the radioactive isotope $^{14}C$ is 4.5-μm wavelength range. The combined selectivity of the absorption line of the target substance, the light generator, and the optical resonator mode can achieve high sensitivity (detail is omitted).

Throughout the specification, the term "carbon isotope" includes stable isotopes $^{12}C$ and $^{13}C$ and radioactive isotopes $^{14}C$, unless otherwise specified. In the case that the elemental signature "O" indicates a carbon isotope mixture in natural abundance.

Isotopic oxygen includes $^{16}O$, $^{17}O$ and $^{18}O$ and the elemental signature "O" indicates that an isotopic oxygen mixture in natural abundance.

The term "carbon dioxide isotope" includes $^{12}CO_2$, $^{13}CO_2$, and $^{14}CO_2$ unless otherwise specified. The signature "$CO_2$" indicates carbon dioxide molecules composed of carbon isotope and isotopic oxygen each in natural abundance.

Throughout the specification, the term "biological sample" includes blood, plasma, serum, urine, feces, bile, saliva, and other body fluid and secretion; intake gas, oral gas, skin gas, and other biological gas; various organs, such as lung, heart, liver, kidney, brain, and skin, and crushed products thereof. Examples of the origin of the biological sample include all living objects, such as animals, plants, and microorganisms; preferably, mammals, preferably human beings. Examples of mammals include, but should not be limited to, human beings, monkey, mouse, rat, marmot, rabbit, sheep, goat, horse, cattle, hog, canine, and cat.

<Carbon Dioxide Isotopic Generator>

The carbon dioxide isotope generator 40 may be of any type that can convert carbon isotope to carbon dioxide isotope. The carbon dioxide isotope generator 40 should preferably have a function to oxidize a sample and to convert carbon contained in the sample to carbon dioxide.

Figure 2:
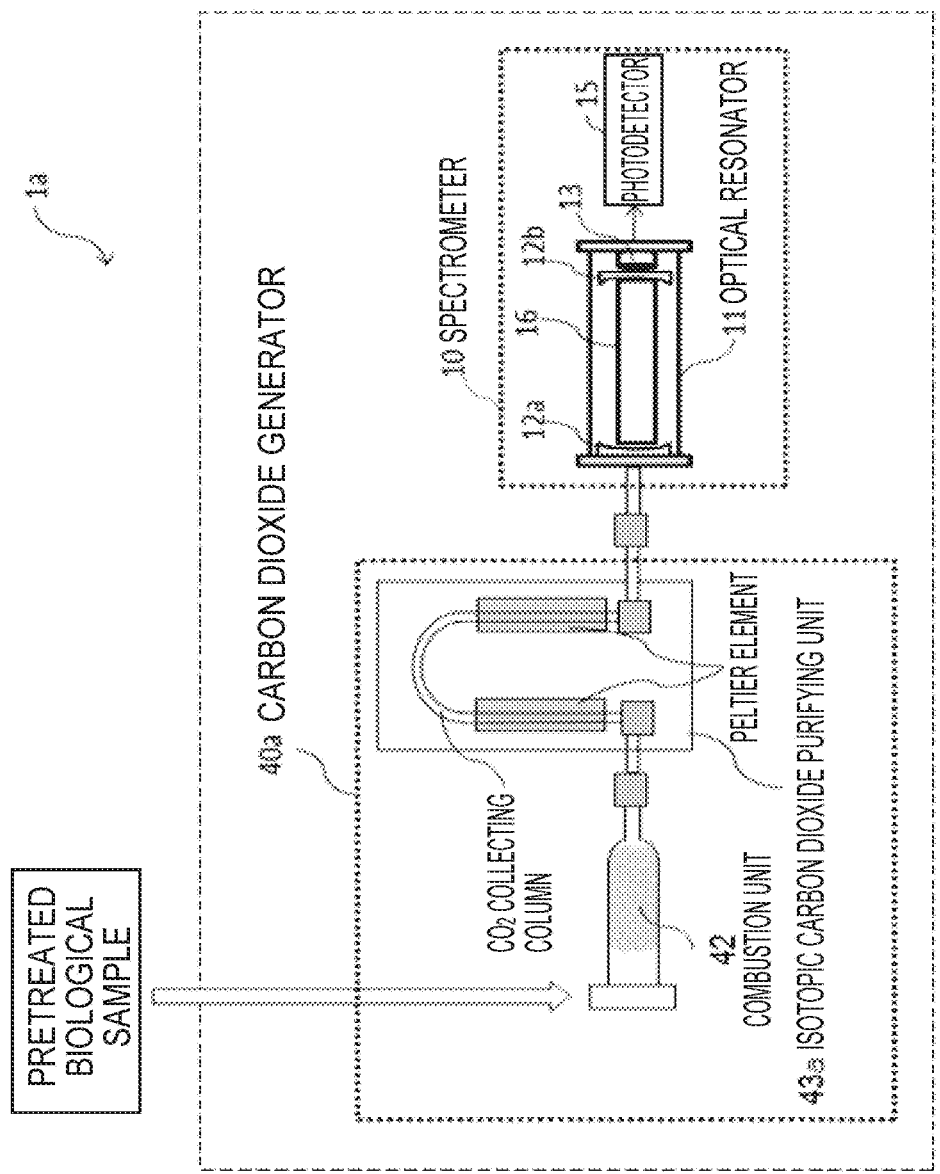
FIG. 2 is a conceptual view of the embodiment a of a carbon dioxide isotope generator.
Figure 3:
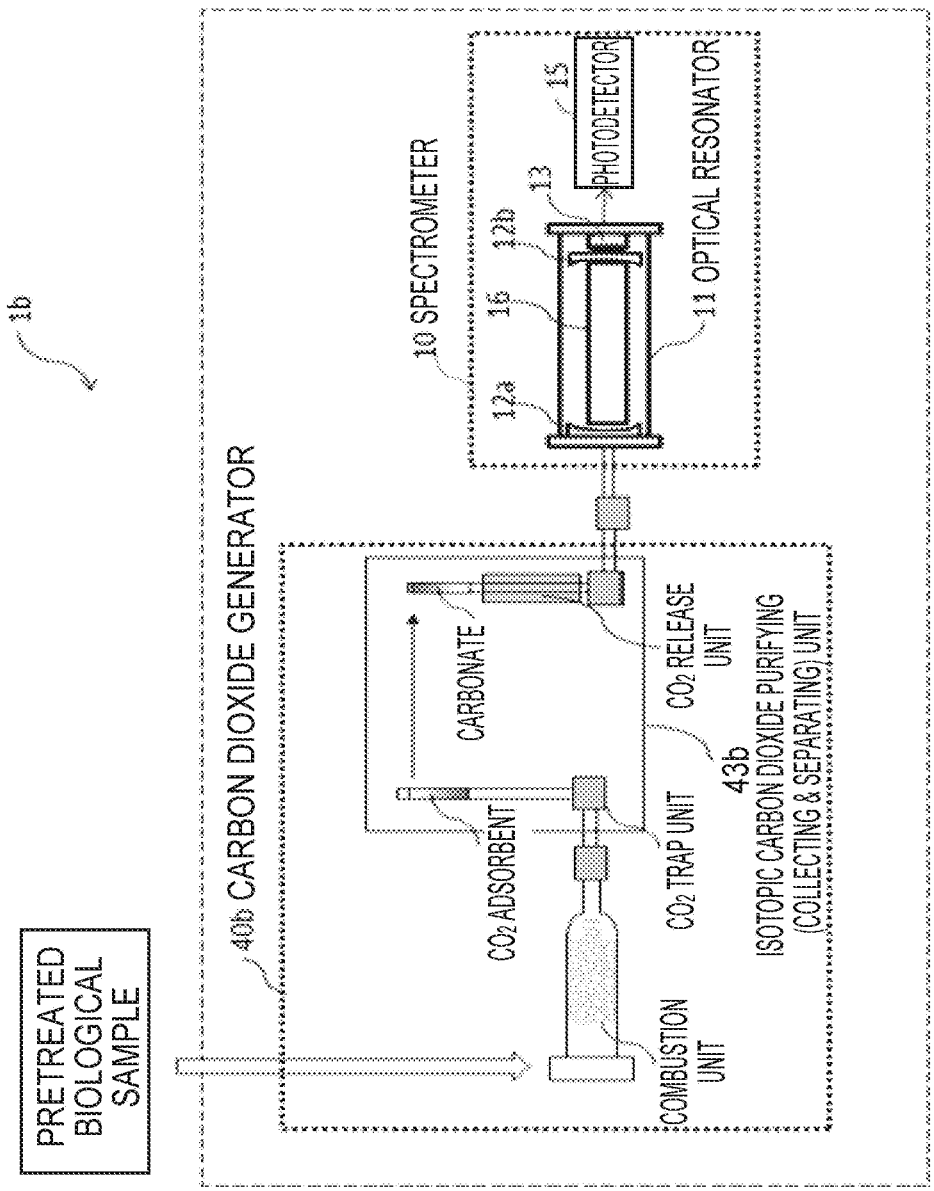
FIG. 3 is a conceptual view of the embodiment b of a carbon dioxide isotope generator.

The carbon dioxide isotope generator 40 may be a carbon dioxide generator (G) 41, for example, a total organic carbon (TOC) gas generator, a sample gas generator for gas chromatography, a sample gas generator for combustion ion chromatography, or an elemental analyzer (EA). In other embodiments, carbon dioxide generators 40a and 40b can also be employed as shown in FIGS. 2 and 3.

Figure 4:
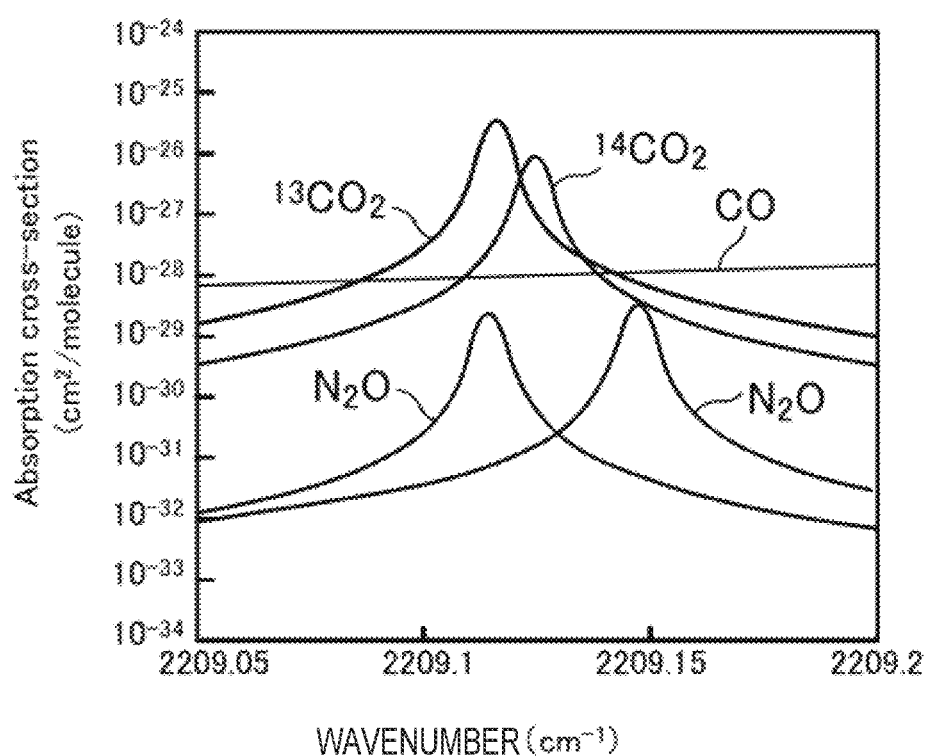
FIG. 4 illustrates absorption spectra in the 4.5-µm wavelength range of $^{14}CO_2$ and contaminant gases.

FIG. 4 is 4.5-μm wavelength range absorption spectra of $^{14}CO_2$ and competitive gases $^{13}CO_2$, CO, and $N_2O$ under the condition of a $CO_2$ partial pressure 20% of a CO partial pressure of $1.0\times10^{-4}$% a $N_2O$ partial pressure of $3.0\times10^{-8}$% at 273K.

Gas containing carbon dioxide isotope $^{14}CO_2$ (hereinafter merely $^{14}CO_2$) can be generated through combustion of a pretreated biological sample; however, gaseous contaminants, such as CO and $N_2O$ are generated together with $^{14}CO_2$ in this process. CO and $N_2O$ each exhibit a 4.5-μm band absorption spectrum as shown in FIG. 4 and interfere with the 4.5-μm wavelength range absorption spectrum assigned to $^{14}CO_2$. Thus, Co and $N_2O$ should preferably be removed for improved analytical sensitivity.

A typical process of removing CO and $N_2O$ involves collection and separation of $^{14}CO_2$ as described below. The process may be combined with a process of removing or reducing CO and $N_2O$ with an oxidation catalyst or platinum catalyst.

(i) Collection and Separation of $^{14}CO_2$ Thermal Desorption Column

FIG. 2 is a conceptual view of Embodiment a of a carbon dioxide isotope generator. The carbon dioxide isotope generator 40a includes a combustion unit 42 and a carbon dioxide isotope purifying unit 43a.

The combustion unit 42 includes a combustion tube and a heater (not depicted) to heat the combustion tube. The combustion tube is composed of refractory glass (such as quartz glass) to contain a sample therein and has a sample port (not shown). Besides the sample port, the combustion tube may have a carrier gas port through which carrier gas can be introduced. Alternatively, a sample introducing unit of a separate component having a sample port and a carrier gas port may be provided at an end of the combustion port.

Examples of the heater include electric furnaces, specifically tubular electric furnaces that can place and heat a combustion tube therein. A typical example of the tubular electric furnace is ARF-30M available from (Asahi Rika Seisakusho).

The combustion tube should preferably be provided with an oxygen unit and/or a reduction unit packed with at least one catalyst downstream of the carrier gas channel. The oxygen unit and/or reduction unit may be provided at one end of the combustion tube or provided in the form of a separate component. Examples of the catalyst to be contained in the oxygen unit include copper oxide and a mixture of silver and cobalt oxide. The oxidation unit can oxidize $H_2$ and CO generated by combustion of a sample into $H_2O$ and $CO_2$. Examples of the catalyst to be contained in the reduction unit include reduced copper, and a platinum catalyst. The reduction unit can reduce nitrogen oxides (NOx) containing $N_2O$ into $N_2$.

The carbon dioxide isotope purifying unit 43a may be a thermal desorption column ($CO_2$ collecting column) used for gas chromatography. This column can adsorb $^{14}CO_2$ in the gas generated by combustion of a biological sample. The detection of $^{14}CO_2$ is less affected or completely unaffected by CO and $N_2O$. Thus, the $CO_2$ gas containing $^{14}CO_2$ is temporally collected in the GC column, it is expected that the $CO_2$ gas containing $^{14}CO_2$ is concentrated. Finally it is expected that the partial pressure of the $^{14}CO_2$ gas increases.

(ii) Separation of $^{14}CO_2$ Through Trapping of $^{14}CO_2$ on a $^{14}CO_2$ Adsorbent and Discharge Therefrom FIG. 3 is a conceptual view of Embodiment b of a carbon dioxide isotope generator. The carbon dioxide isotope generator 40b includes a combustion unit and a carbon dioxide isotope purifying unit.

The combustion unit may have a similar configuration to that shown in FIG. 2.

The carbon dioxide isotope purifying unit may be composed of a $^{14}CO_2$ adsorbent, such as soda lime or calcium hydroxide. This can isolate $^{14}CO_2$ in the form of carbonate and solves the problem on the gaseous contaminant. The sample can be temporally reserved in the form of carbonate ($^{14}CO_2$). The carbon dioxide isotope can be released with phosphoric acid.

The gaseous contaminant can thereby be removed through Process (i) and/or Process (ii).

(iii) Concentration (Separation) of $^{14}CO_2$ $^{14}CO_2$ generated by combustion of the biological sample is diffused in piping. $^{14}CO_2$ may be adsorbed to be concentrated on an adsorbent to enhance the detection sensitivity. Such concentration will separate $^{14}CO_2$ from CO and $N_2O$.

<Spectrometer>

With reference to FIG. 1, the spectrometer 10 includes an optical resonator 11 and a photodetector 15 that determines the intensity of the light transmitted from the optical resonator 11. The optical resonator or optical cavity 11 includes a cylindrical body to be filled with the target carbon dioxide isotope; a pair of highly reflective mirrors 12a and 12b (reflectance: 99.99% or more) respectively disposed at first and second longitudinal ends of the body such that the concave faces of the mirrors confront each other; a piezoelectric element 13 disposed at the second end of the body to adjust the distance between the mirrors 12a and 12b; and a cell 16 to be filled with an analyte gas. Although not illustrated, the side of the body is preferably provided with a gas inlet through which the carbon dioxide isotope is injected and a port for adjusting the pressure in the body.

A laser beam incident on and confined in the optical resonator 11 repeatedly reflects between the mirrors over several thousand to ten thousand times while the optical resonator 11 emits light at an intensity corresponding to the reflectance of the mirrors. Thus, the effective optical path length of the laser beam reaches several tens of kilometers, and a trace amount of analyte gas contained in the optical resonator can yield large absorption intensity.

Figure 5A:
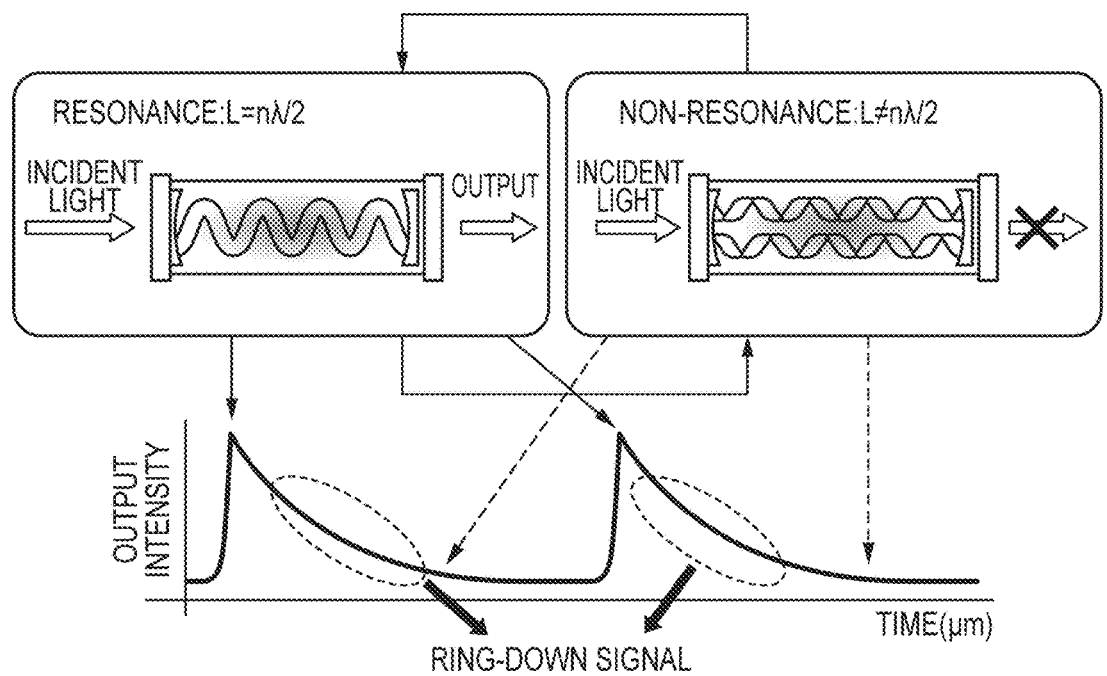
FIGS. 5A and 5B illustrate the principle of high-rate scanning cavity ring down absorption spectroscopy (CRDS) using laser light.
Figure 5B:
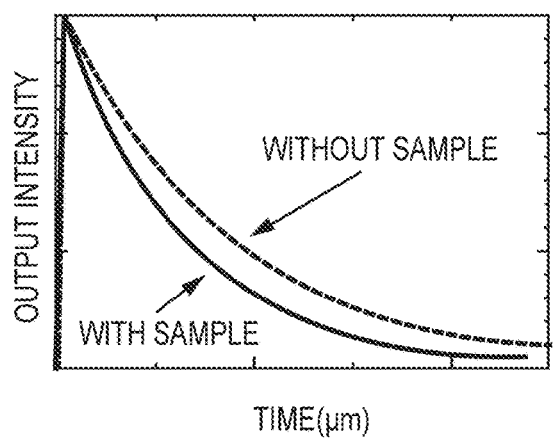

FIGS. 5A and 5B illustrate the principle of laser-based high-speed cavity ring-down spectroscopy (hereinafter may be referred to as "CRDS").

As illustrated in FIG. 5A, the optical resonator in a resonance state between the mirrors outputs a high-intensity signal. In contrast, the resonator outputs no signal due to optical interference in a non-resonance state caused by a perturbation in distance between the mirrors through operation of the piezoelectric element 13. Thus, an exponential decay signal (ring-down signal) as shown in FIG. 5A is observed through a rapid variation in length of the optical resonator (i.e., a rapid change from the resonance state to the non-resonance state). Such a ring-down signal may be observed by rapid shielding of the incident laser beam with an optical switch 26 (see FIG. 7).

In the case of the absence of a light-absorbing substance in the optical resonator, the dotted curve in FIG. 5B corresponds to a time-dependent ring-down signal output from the optical resonator. In contrast, the solid curve in FIG. 5B corresponds to the case of the presence of a light-absorbing substance in the optical resonator. In this case, the light decay time is shortened because of absorption of the laser beam by the light-absorbing substance during repeated reflection of the laser beam in the optical resonator. The light decay time depends on the concentration of the light-absorbing substance in the optical resonator and the wavelength of the incident laser beam. Thus, the absolute concentration of the light-absorbing substance can be calculated based on the Beer-Lambert law ii. The concentration of the light-absorbing substance in the optical resonator may be determined through measurement of a modulation in ring-down rate, which is proportional to the concentration of the light-absorbing substance.

The light leaked from the optical resonator is detected with the photodetector, and the concentration of $^{14}CO_2$ is calculated with the arithmetic device. The concentration of $^{14}C$ is then calculated from the concentration of $^{14}CO_2$.

Figure 10:
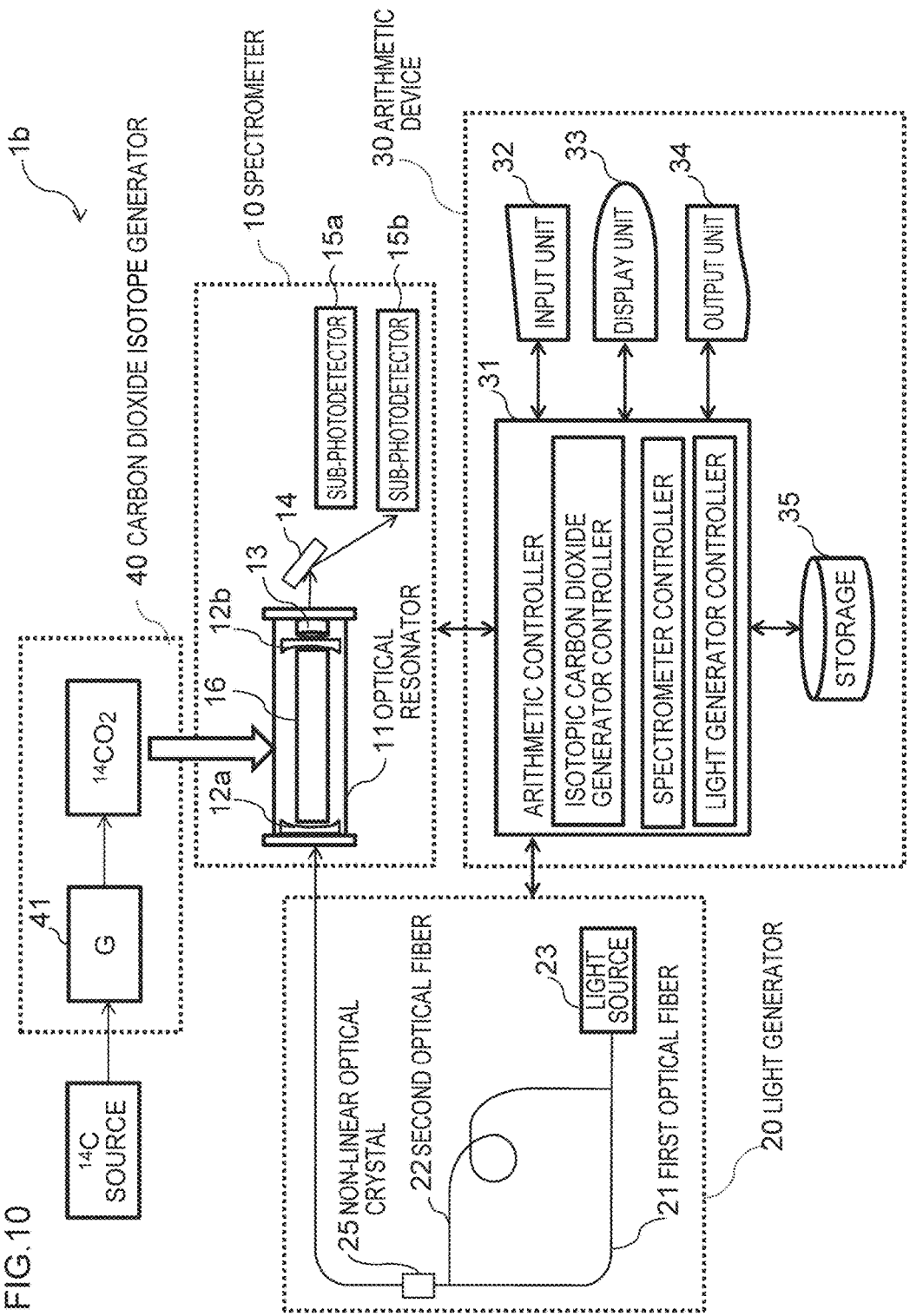
FIG. 10 is a conceptual view of a carbon isotope analyzer according to Modification 2.

The photodetector may be used in combination with a diffraction grating 14 that detects light having a specific wavelength (see FIG. 10). Details will be described below together with the light generator.

The distance between the mirrors 12*a* and 12*b* in the optical resonator 11, the curvature radius of the mirrors 12*a* and 12*b*, and the longitudinal length and width of the body should preferably be varied depending on the absorption wavelength of the carbon dioxide isotope (i.e., analyte). The length of the optical resonator is adjusted from 1 mm to 10 m, for example.

In the case of carbon dioxide isotope $^{14}CO_2$, an increase in length of the optical resonator contributes to enhancement of the effective optical path length, but leads to an increase in volume of the gas cell, resulting in an increase in amount of a sample required for the analysis. Thus, the length of the optical resonator is preferably 10 cm to 60 cm. Preferably, the curvature radius of the mirrors 12*a* and 12*b* is equal to or slightly larger than the length of the optical resonator.

The distance between the mirrors can be adjusted by, for example, several micrometers to several tens of micrometers through the drive of the piezoelectric element 13. The distance between the mirrors can be finely adjusted by the piezoelectric element 13 for preparation of an optimal resonance state. The mirrors 12*a* and 12*b* (i.e., a pair of concave mirrors) may be replaced with combination of a concave mirror and a planar mirror or combination of two planar mirrors that can provide a sufficient optical path.

The mirrors 12*a* and 12*b* may be composed of sapphire glass.

The cell 16 to be filled with the analyte gas preferably has a small volume because even a small amount of the analyte effectively provides optical resonance. The volume of the cell 16 may be 8 mL to 1,000 mL. The cell volume can be appropriately determined depending on the amount of a $^{14}C$ source to be analyzed. For example, the cell volume is preferably 80 mL to 120 mL for a $^{14}C$ source that is available in a large volume (e.g., urine), and is preferably 8 mL to 12 mL for a $^{14}C$ source that is available only in a small volume (e.g., blood or teat fluid).

Evaluation of Stability Condition of Optical Resonator

The $^{14}CO_2$ absorption and the detection limit of CRDS were calculated based on spectroscopic data. Spectroscopic data on $^{12}CO_2$ and $^{13}CO_2$ were retrieved from the high-resolution transmission molecular absorption database (HITRAN), and spectroscopic data on $^{14}CO_2$ were extracted from the reference "S. Dobos, et al., Z. Naturforsch, 44a, 633-639 (1989)."

A Modification ($\Delta\beta$) in ring-down rate (exponential decay rate) caused by $^{14}CO_2$ absorption ($\Delta\beta=\beta-\beta_0$ where $\beta$ is a decay rate in the presence of a sample, and $\beta_0$ is a decay rate in the absence of a sample) is represented by the following expression:

$$\Delta\beta = \sigma_{14}(\lambda,T,P)N(T,P,X_{14})c$$

where $\sigma_{14}$ represents the photoabsorption cross section of $^{14}CO_2$, N represents the number density of molecules, represents the speed of light, and $\sigma_{14}$ and N are the function of $\lambda$ (the wavelength of laser beam), T (temperature), P (pressure), and $X_{14}$=ratio $^{14}C/^{Total}C$)

Figure 6:
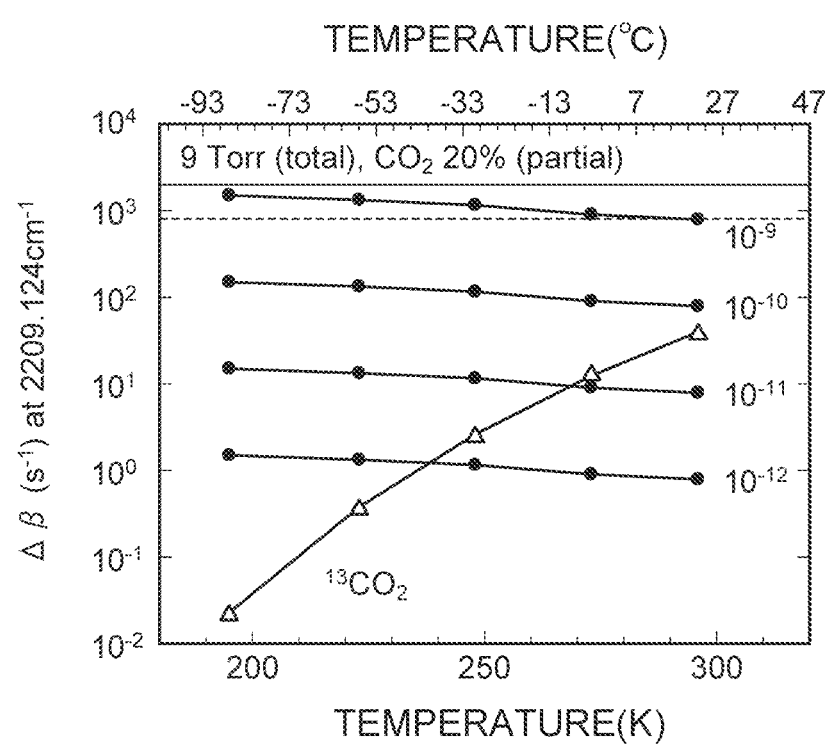
FIG. 6 illustrates the dependence of CRDS absorption $\Delta\beta$ of $^{13}CO_2$ and $^{14}CO_2$ on temperature.

FIG. 6 illustrates the dependence of calculated $\Delta\beta$ due to $^{13}CO_2$ absorption or $^{14}CO_2$ absorption on temperature. As illustrated in FIG. 6, $^{13}CO_2$ absorption is equal to or higher than $^{14}CO_2$ absorption at 300K (room temperature) at a $^{14}C/^{Total}C$ of $10^{-10}$, $10^{-11}$, or $10^{-12}$, and thus the analysis requires cooling in such a case.

If a Modification ($\Delta\beta_0$) in ring-down rate (corresponding to noise derived from the optical resonator) can be reduced to a level on the order of $10^1$ $s^{-1}$, the analysis could be performed at a ratio $^{14}C/^{Total}C$ on the order of $10^{-11}$. Thus, cooling at about −40° C. is required during the analysis. In the case of a ratio $^{14}C/^{Total}C$ of $10^{-11}$ as a lower detection limit, the drawing suggests that requirements involve an increase (for example, 20%) in partial pressure of $CO_2$ gas due to concentration of the $CO_2$ gas and the temperature condition described above.

The cooler used in the analysis and the cooling temperature will be detailed below in Modification 1 of the carbon isotope analyzer.

<Light Generator>

The light generator 20 may be of any type that can generate light having the absorption wavelength of the carbon dioxide isotope. In this embodiment, a compact light generator will be described that can readily generates light of a 4.5-μm wavelength range, which is the absorption wavelength of carbon dioxide isotope $^{14}CO_2$ The light generator 20 includes a single light source 23, two optical fibers, i.e., a first optical fiber 21 and a second optical fiber 22 that generates light beams having different frequencies from the light source "23, and a non-linear optical crystal 25 that generates light having the absorption wavelength of the carbon dioxide isotope from a difference in frequency between the light beams transmitted through the optical crystal.

A preferred light source 23 is a short-wavelength pulse generator that can generate comb-shaped light fluxes of different wavelengths at regular intervals (hereinafter may be referred to as "optical comb"). In the case that the light source is a continuous wave generator, the wavelength width increases at the center of each light flux, precluding generation of comb-shaped light fluxes of different wavelengths at regular intervals.

Examples of the light source 23 include a solid-state laser, a semiconductor laser, and a fiber laser that generate short pulses by mode locking. Particularly preferred is a fiber laser, which is a compact and practical light source having high environmental stability.

Examples of usable fiber lasers include an erbium (Er) fiber laser (1.55 μm beam) and an ytterbium (Yb) fiber laser (1.04 μm beam). An Er fiber laser is preferred from the economical viewpoint, whereas an Yb fiber laser is preferred in view of enhanced optical intensity.

The first optical fiber 21 transmits a light beam from the light source. The second optical fiber 22 for wavelength conversion splitting from the first optical fiber 21 at a splitting node and coupling with the first optical fiber 21 at a coupling node downstream of the splitting node. The first optical fiber 21 may extend from the light source to the optical resonator.

The downstream end of the first optical fiber 21 should preferably abut on the mirror 12a. In such a case, the light transmitted from the optical resonator 11 is not exposed to air, resulting an increase in accuracy of measurement of the intensity of the transmitted light.

It is preferred that the first optical fiber 21 can transmit high intensity of ultrashort light pulses without deterioration of the optical properties of the pulses. The first optical fiber 21 should preferably be composed of fused silica.

It is preferred that the second optical fiber 22 have anomalous dispersion and efficiently generate long-wavelength ultrashort pulses by stimulated Raman scattering and the soliton effect. Examples of the second optical fiber 22 include a polarization-maintaining fiber, a single-mode fiber, a photonic crystal fiber, and a photonic bandgap fiber. The optical fiber should preferably have a length of several meters to several hundred meters depending on the wavelength shift. The second optical fiber 22 should preferably be composed of fused silica.

Examples of usable non-linear optical crystal 25 include PPMGSLT (periodically poled MgO-doped stoichiometric lithium tantalite ($LiTaO_3$)) crystals, PPLN (periodically poled lithium niobate) crystals, and GaSe (gallium selenide) crystals, which crystals can readily emit light of a 4.5-μm wavelength range. Since a single fiber laser light source is used, perturbation of optical frequency can be cancelled out in difference frequency generation as described below.

Difference frequency generation (hereinafter referred to as "DFG") can be used to generate difference-frequency light. In detail, the light beams of different frequencies (wavelengths) from the first and second optical fibers 21 and 22 transmit through the non-linear optical crystal, to generate difference-frequency light based on the difference in frequency. Thus, two light beams having wavelengths $\lambda_1$ and $\lambda_2$ are generated with the single light source 23 and propagate through the non-linear optical crystal, to generate light in the 4.5-μm wavelength range (i.e., the absorption wavelength of the carbon dioxide isotope) based on the difference in frequency. The conversion efficiency of the DFG using the non-linear optical crystal depends on the photon density of light beams having different wavelengths ($\lambda_1, \lambda_2, \ldots \lambda_x$). Thus, difference-frequency light can be generated from a single pulse laser light source through DFG.

The resultant 4.5-μm wavelength range light is an optical comb composed of a spectrum of frequencies (modes) with regular intervals ($f_r$) each corresponding to one pulse (frequency $f=f_{ceo}+N \cdot f_r$, N: mode number). CRDS using the optical comb requires extraction of light having the absorption wavelength of the analyte.

In the case of the carbon isotope analyzer disclosed in Non-Patent Document 1 by I. Galli, et al., laser beams having different wavelengths are generated from two laser devices, and light having the absorption wavelength of the carbon dioxide isotope is generated based on the difference in frequency between these laser beams. Thus, the analyzer has a large size and requires a complicated operation. Since the two beams generated from the two light sources exhibit different widths and timings of perturbation, it is difficult to reduce the perturbation of light composed of the two beams. Thus, the analyzer should be provided with a device for controlling the perturbation of light. In contrast, the light generator according to the embodiment of the present invention includes a single fiber laser light source, optical fibers having a length of several meters, and a non-linear optical crystal. Thus, the light generator has a small size and is easy to carry and operate. Since two light beams are generated from a single light source, these beams exhibit the same width and timing of perturbation, and thus the perturbation of optical frequency can be readily cancelled through difference frequency generation without a perturbation controller.

In some embodiments, a laser beam may be transmitted through air between the optical resonator and the coupling node of the first optical fiber with the second optical fiber. Alternatively, the optical path between the optical resonator and the combining point may optionally be provided with an optical transmission device including an optical system for convergence and/or divergence of a laser beam through a lens. In a more preferred embodiment, the entire optical path between the light source and the optical resonator is composed of an optical fiber to prevent scattering and absorption of a laser beam in air and to reduce the deviation of the optical axis. Such a configuration can stabilize the device.

In some embodiments, light may be transmitted between the optical resonator and the detector through a space or an optical fiber.

<Arithmetic Device>

The arithmetic device 30 may be of any type that can determine the concentration of a light-absorbing substance in the optical resonator based on the decay time and ring-down rate and calculate the concentration of the carbon isotope from the concentration of the light-absorbing substance.

The arithmetic device 30 includes an arithmetic controller 31, such as an arithmetic unit used in a common computer system (e.g., CPU); an input unit 32, such as a keyboard or a pointing device (e.g., a mouse); a display unit 33, such as an image display (e.g., a liquid crystal display or a monitor); an output unit 34, such as a printer; and a memory unit 35, such as a ROM, a RAM, or a magnetic disk.

<Cooler and a Dehumidifier>

A cooler and a dehumidifier (not shown in FIG. 1) may be provided. Dehumidification may be carried out with a cooling means, such as a Peltier device or by membrane separation using a polymer membrane, such as a fluorinated ion-exchange membrane, for removing moisture. Details will be described in items "Modifications" and "Analytical method" later.

In the case that the carbon isotope analyzer 1 is used in a microdose test, the prospective detection sensitivity to the radioactive carbon isotope $^{14}C$ is approximately 0.1 dpm/ml. Such a detection sensitivity "0.1 dpm/ml" requires not only use of "narrow-spectrum laser" as a light source, but also the stability of wavelength or frequency of the light source. In other words, the requirements include no deviation from the wavelength of the absorption line and a narrow line width. In this regard, the carbon isotope analyzer 1, which involves CRDS with a stable light source using "frequency comb light", can solve such a problem. The carbon isotope analyzer 1 has an advantage in that the analyzer can determine a low concentration of radioactive carbon isotope in the analyte.

The earlier literature (Hiromoto Kazuo et al., "Designing of $^{14}C$ continuous monitoring based on cavity ring down spectroscopy", preprints of Annual Meeting, the Atomic Energy Society of Japan, Mar. 19, 2010, p. 432) discloses determination of the concentration of $^{14}C$ in carbon dioxide by CRDS in relation to monitoring of the concentration of spent fuel in atomic power generation. Although the signal processing using the fast Fourier transformation (FFT) disclosed in the literature has a high processing rate, the fluctuation of the baseline increases, and thus a detection sensitivity of 0.1 dpm/ml cannot be readily achieved.

Although the carbon isotope analyzer of the present invention has been described with reference to the embodiment, the configuration of the carbon isotope analyzer should not be limited to the analyzer described above, and various modifications may be made. Several modifications of the carbon isotope analyzer will now be described by focusing on modified points.

(Modification 1 of Carbon Isotope Analyzer)

Figure 7:
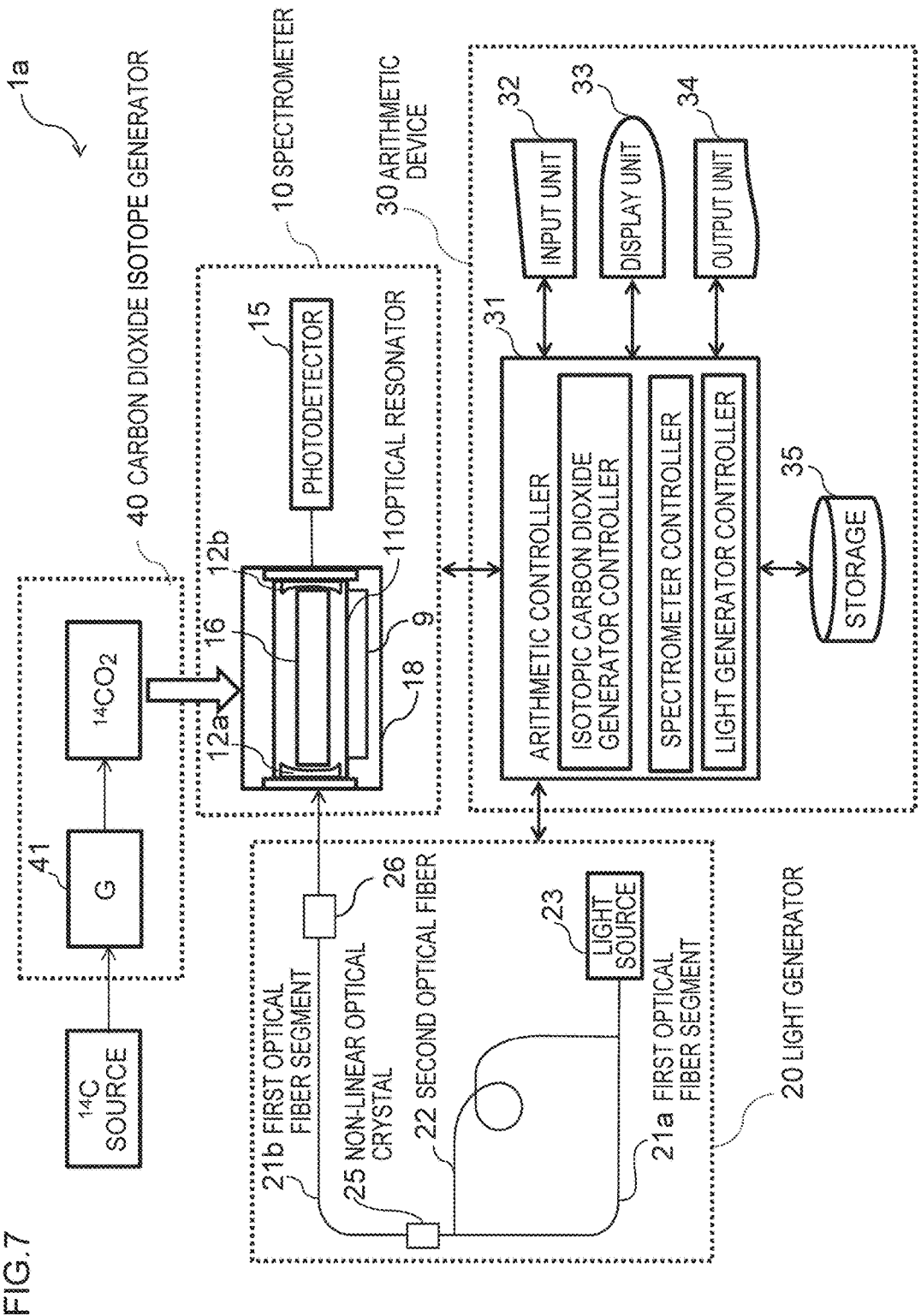
FIG. 7 is a conceptual view of a carbon isotope analyzer according to Modification 1.

FIG. 7 is a schematic illustration of modification 1 of the carbon isotope analyzer. As illustrated in FIG. 7, the spectrometer 1a may further include a Peltier element 19 for cooling the optical resonator 11 and a vacuum unit 18 accommodating the optical resonator 11. Since the light absorption of $^{14}CO_2$ has temperature dependence, a decrease in temperature in the optical resonator 11 with the Peltier element 19 facilitates distinction between $^{14}CO_2$ absorption lines and $^{13}CO_2$ and $^{12}CO_2$ absorption lines and enhances the $^{14}CO_2$ absorption intensity. The optical resonator 11 disposed in the vacuum unit 18 is not exposed to external air, leading to a reduction in effect of the external temperature on the resonator 11 and an improvement in analytical accuracy.

The cooler for cooling the optical resonator 11 may be, for example, a liquid nitrogen vessel or a dry ice vessel besides the Peltier element 19. The Peltier element 19 is preferred in view of a reduction in size of the spectrometer 10, whereas a liquid nitrogen vessel or a dry ice vessel is preferred in view of a reduction in production cost of the analyzer.

The vacuum unit 18 may be of any type that can accommodate the optical resonator 11, apply light from the light generator 20 to the optical resonator 11, and transmit light to the photodetector.

Figure 8:
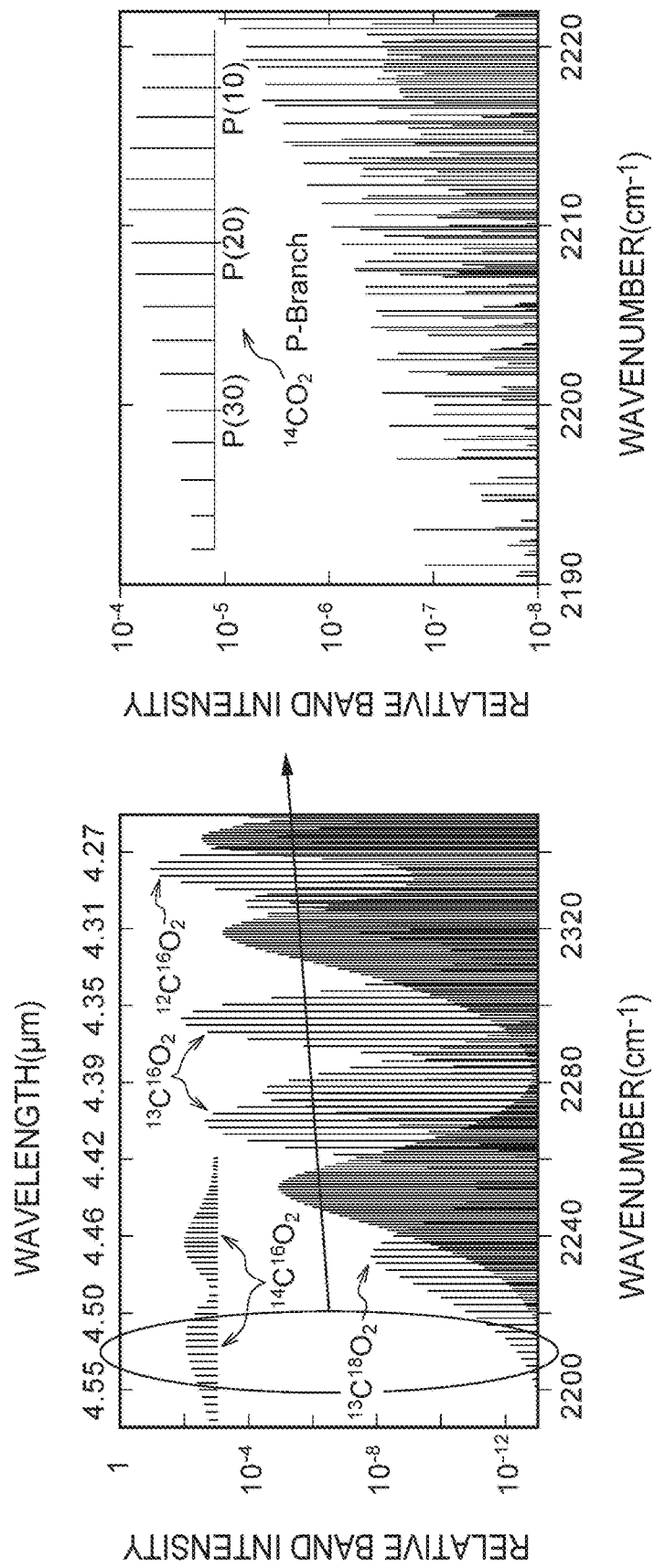
FIG. 8 illustrates the relation between the absorption wavelength and the absorption intensity of an analytical sample.

FIG. 8 (cited from Applied Physics Vol. 24, pp. 381-386, 1981) illustrates the relationship between the absorption wavelength and absorption intensity of analytes $^{12}C^{16}O_2$, $^{13}C^{18}O_2$, $^{13}C^{16}O_2$, and $^{14}C^{16}O_2$. As illustrated in FIG. 8, each carbon dioxide isotope has distinct absorption lines. Actual absorption lines have a finite width caused by the pressure and temperature of a sample. Thus, the pressure and temperature of a sample are preferably adjusted to atmospheric pressure or less and 273K (0° C.) or less, respectively.

Since the absorption intensity of $^{14}CO_2$ has temperature dependence as described above, the temperature in the optical resonator 11 is preferably adjusted to a minimum possible level. In detail, the temperature in the optical resonator is preferably adjusted to 273K (0° C.) or less. The temperature may have any lower limit. In view of cooling effect and cost, the temperature in the optical resonator 11 is adjusted to preferably 173K to 253K (−100° C. to −20° C.), more preferably about 233K (−40° C.).

The spectrometer may further be provided with a vibration damper. The vibration damper can prevent a perturbation in distance between the mirrors due to the external vibration, resulting in an improvement in analytical accuracy. The vibration damper may be an impact absorber (polymer gel) or a seismic isolator. The seismic isolator may be of any type that can provide the spectrometer with vibration having a phase opposite to that of the external vibration.

Figure 9:
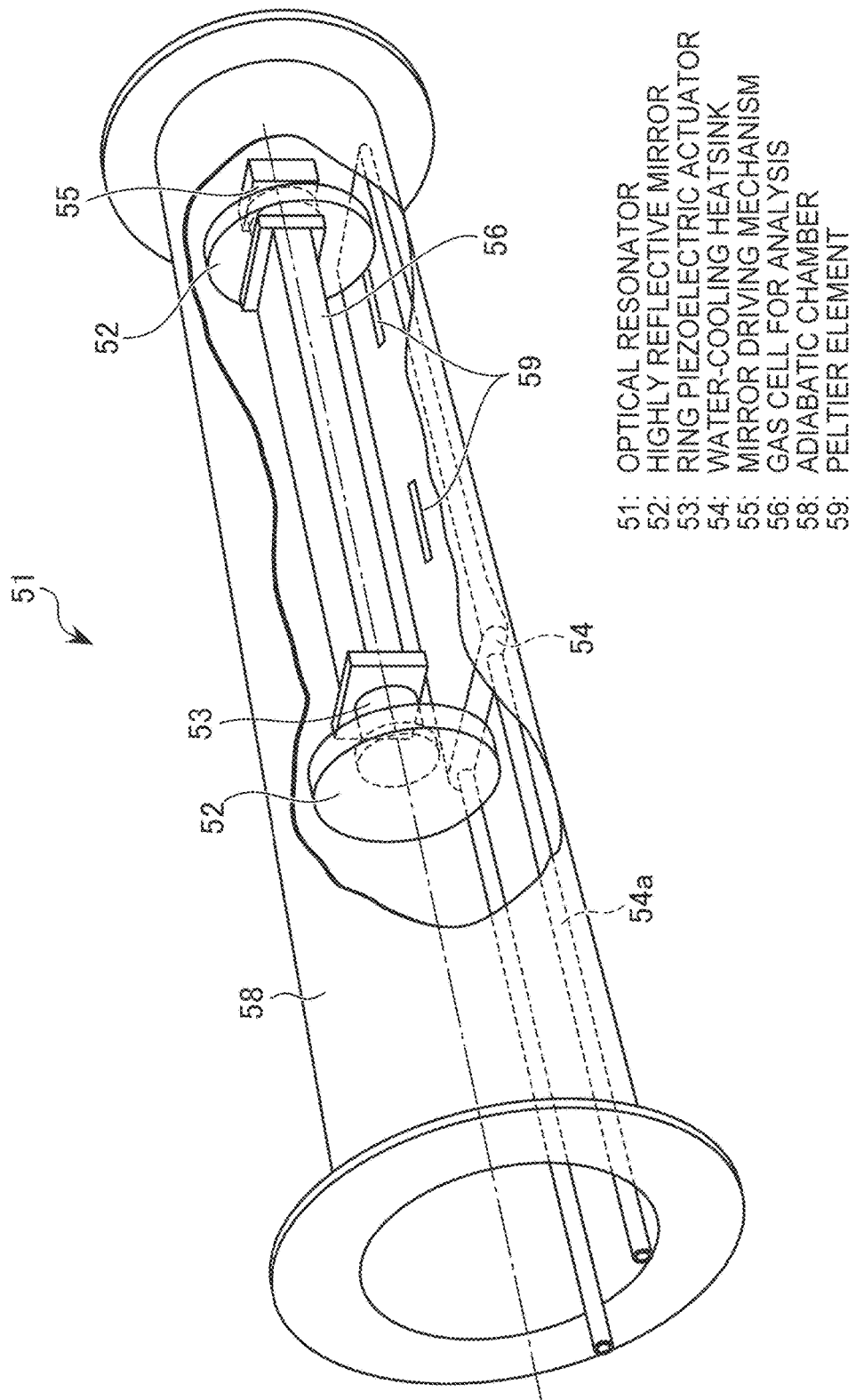
FIG. 9 is a conceptual view of a Modification of the optical resonator.

FIG. 9 is a schematic illustration (partially cross-sectional view) of a modification of the optical resonator 11. As illustrated in FIG. 9, an optical resonator 51 includes a cylindrical adiabatic chamber (vacuum device) 58; a gas cell 56 for analysis disposed in the adiabatic chamber 58; a pair of highly reflective mirrors 52 disposed at two ends of the gas cell 56; a mirror driving mechanism 55 disposed at one end of the gas cell 56; a ring piezoelectric actuator 53 disposed on the other end of the gas cell 56; a Peltier element 59 for cooling the gas cell 56; and a water-cooling heatsink 54 provided with a cooling pipe 54a connected to a circulation coiler (not shown).

<Light Shield>

In the aforementioned embodiment, the distance between the mirrors is adjusted with the piezoelectric element 13 for generation of ring-down signals in the spectrometer 10. For generation of ring-down signals, a light shield may be provided in the light generator 20 for ON/OFF control of light incident on the optical resonator 11. The light shield may be of any type that can promptly block light having the absorption wavelength of the carbon dioxide isotope. The light shield is, for example, an optical switch 26 illustrated in FIG. 7. The excitation light should be blocked within a time much shorter than the decay time of light in the optical resonator.

In the aforementioned embodiment, the first optical fiber 21 extends from the light source 23 to the optical resonator 11. Alternatively, the first optical fiber 21 may be composed of a first fiber segment 21a extending between the light source 23 and the non-linear optical crystal 25 and a second fiber segment 21b for mid-infrared light extending between the non-linear optical crystal 25 and the optical resonator 11. The second fiber segment 21b can effectively transmit 4.5-μm wavelength range light from the non-linear optical crystal to the optical resonator 11.

The first fiber segment 21a may be of the same type as that of the first optical fiber 21. The second fiber segment 21b may be any mid-infrared optical fiber that barely absorbs 4.5-μm wavelength range light. The second fiber segment 21b is preferably a fluoride fiber or a hollow fiber.

The light generator 20 may be provided with a light transmitter for transmitting light from the non-linear optical crystal 25 to the optical resonator 11 instead of the second fiber segment 21b illustrated in FIG. 7. The light transmitter may be composed of, for example, a combination or module of one or more optical lenses and an optical path composed of optical lenses disposed upstream and/or downstream of the non-linear optical crystal.

(Modification 2 of Carbon Isotope Analyzer)

FIG. 10 is a conceptual view of Modification 2 of the carbon isotope analyzer. As shown in FIG. 10, the spectrometer 1d may further include a diffraction grating 14 for dispersing the transmitted light into spectral components of different wavelengths. In such a case, the photodetector should preferably include a sub-photodetector 15a and a sub-photodetector 15b detecting spectral components having different wavelengths. The spectral components having different wavelengths of the transmitted light can improve the analytical accuracy.

The $^{14}C$ concentration of a sample gas may be determined from the intensity of only necessary absorption lines observed through selection of predetermined light with the optical resonator and selection of wavelengths of transmitted light with the diffraction grating. The diffraction grating disposed in the spectrometer contributes to a further improvement in analytical accuracy.

(Modification 3 of Carbon Isotope Analyzer)

The light generator 20 introduces different light beams from the first optical fiber 21 and the second optical fiber 22 to the nonlinear optical crystal 25 that generates light having the absorption wavelength of carbon dioxide isotope from a difference in frequency. Alternatively, the multiple optical fibers may be replaced with a single optical fiber that generates the light having the absorption wavelength of carbon dioxide isotope with proviso that a difference frequency is available.

Figure 11:
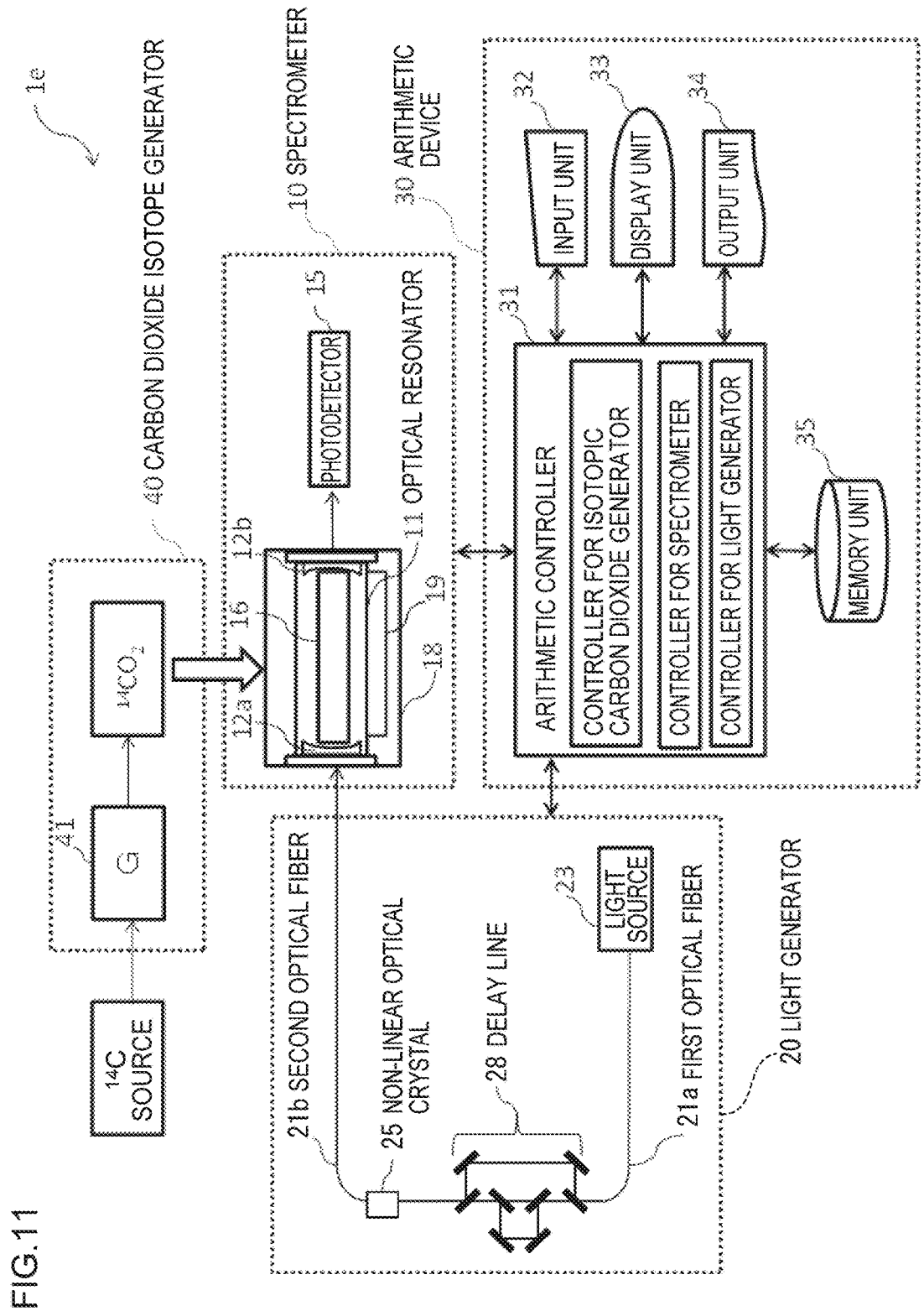
FIG. 11 is a conceptual view of a carbon isotope analyzer according to Modification 3.
Figure 12:
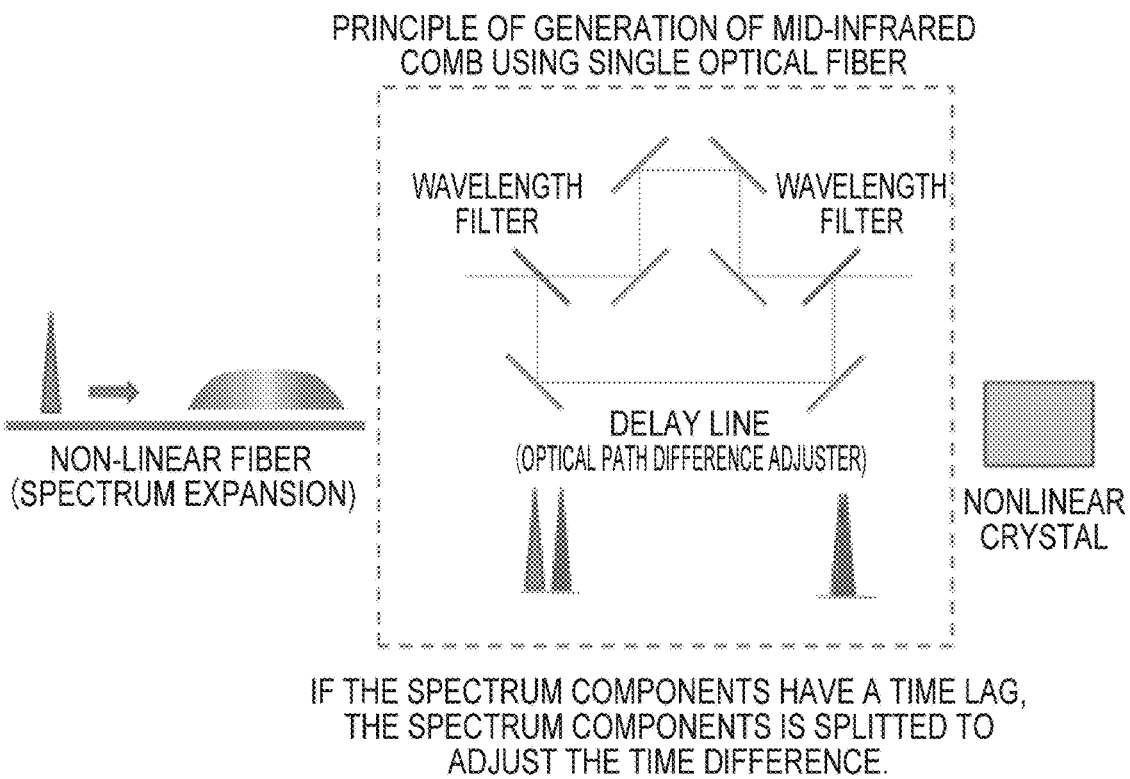
FIG. 12 illustrates the principle of generation of a mid-infrared comb using a single optical fiber.

FIG. 11 is a conceptual view of Modification 3 of the carbon isotope analyzer. FIG. 12 illustrates the principle of generation of a mid-infrared comb using a single optical fiber.

The carbon isotope analyzer 1e shown in FIG. 11 includes a delay line 28 including a plurality of wavelength filters between the light source 23 and the non-linear optical crystal 25. The first optical fiber 21 transmits the light from the light source 23 while expanding the spectrum (spectrum expansion). If the spectrum components have a time lag as shown in FIG. 12, the delay line 28 (optical path difference adjuster) splits the spectrum components depending on the time difference. The spectrum components are focused on the nonlinear crystal 25 to generate the mid-infrared comb.

Any wavelength filter other than the delay line, such as a dispersion medium may also be used.

Figure 13:
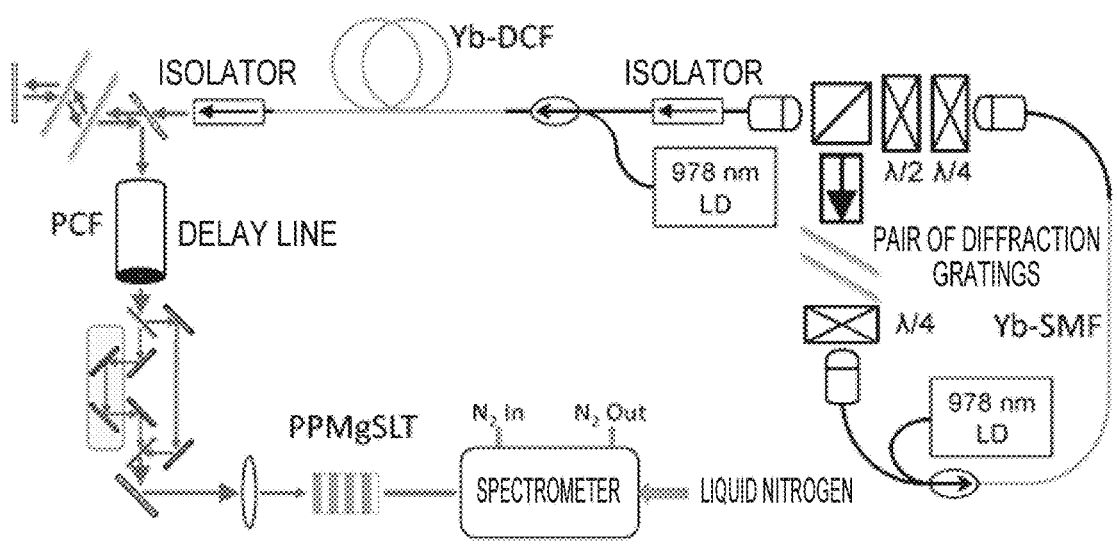
FIG. 13 is a conceptual view of a Modification of the light generator.

FIG. 13 illustrates a modification of the light generator. The light generator shown in FIG. 13 includes a light source; an optical fiber (Yb-DCF) amplifying from the light source; an isolator; a pair of diffraction gratings for compensating for dispersion (time expansion) of the pulsed light transmitted from the isolator; a photonic crystal fiber (hereinafter "PCF") generating broadband light (supercontinuum, hereinafter "SC"); a delay line that splits the light with a wavelength filter or wavelength divider into a plurality of spectrum components, adjusts the time difference between the spectrum components, and focuses predetermined spectrum components on a nonlinear crystal; a nonlinear crystal (PPMGSLT crystal) that generates mid-infrared comb light; and a spectrometer.

In the light generator of FIG. 13 having such a configuration, the time difference between the spectrum components of the light from the light source can be adjusted with a delay line (optical path difference adjuster), so that the predetermined spectrum components without time difference are focused on a nonlinear crystal to generate light with a desired wavelength.

In an example modification of the light generator in FIG. 13, SC light and mid-infrared comb light were generated with a 1.014 μm wavelength range ultrashort pulsed fiber laser light source. The light source was an Yb-doped fiber laser that was mode-locked by nonlinear polarized light rotation and had a pulse repetition rate of 184 MHz. The pulses from the light source were amplified in an Yb-doped double clad fiber with a high-power amplification laser diode with an output of 8 W. The amplified pulses had high chirp values with a central wavelength of 1040 nm and an average output 3 W, and then were compressed into 200 femtoseconds (FWHM) by a pair of diffraction gratings. The SC light was expanded from 900 nm to 1200 nm that was able to be supported by difference frequency generation (DFG) in the mid-infrared region in the optical crystal fiber. The delay line was carefully adjusted during the output from the PCF and the two signals of 900 nm to 1000 nm and 1000 nm to 1200 nm having overlapping space and time were focused on the non-linear optical crystal enabling DFG to the 4.5-μm wavelength range. Experiments were performed with PCFs having dispersion characteristics.

(Example 1)

Figure 14A:
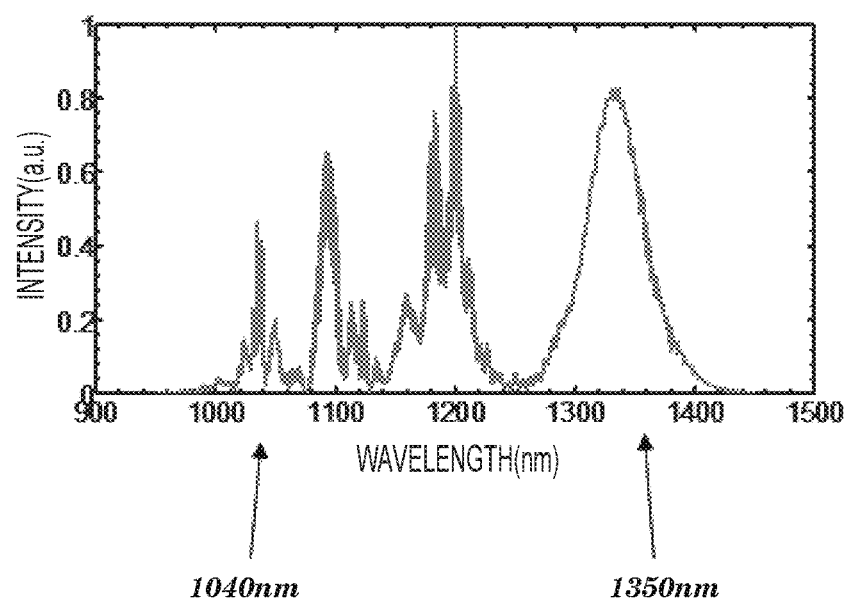
FIG. 14A is a spectrum of the generation of the wavelength shift solitons.
Figure 14B:
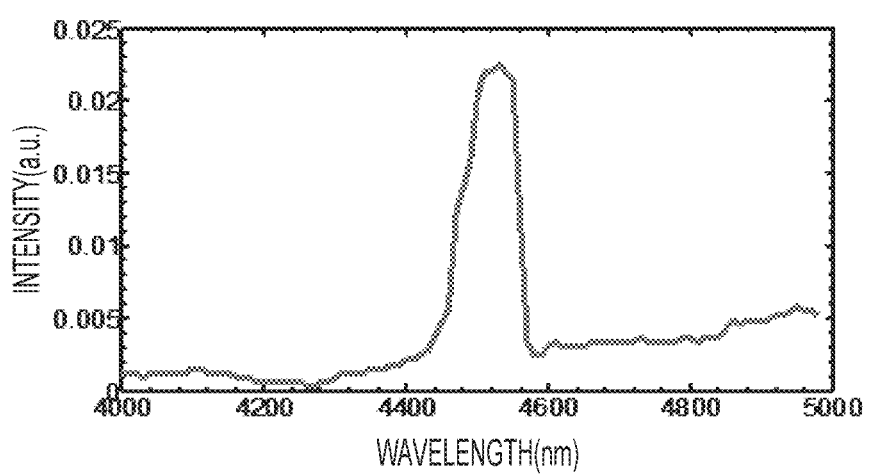
FIG. 14B is a spectrum of a mid-infrared comb.

Using a 20 cm photonic crystal fiber (made by NKT Photonics), which was a PCF with a zero-dispersion wavelength of 1005 nm, the time difference between two spectral components was adjusted with a delay line, and the light was focused on a GaSe crystal. The results are shown in FIGS. 14A and 14B.

(Example 2)

Figure 15A:
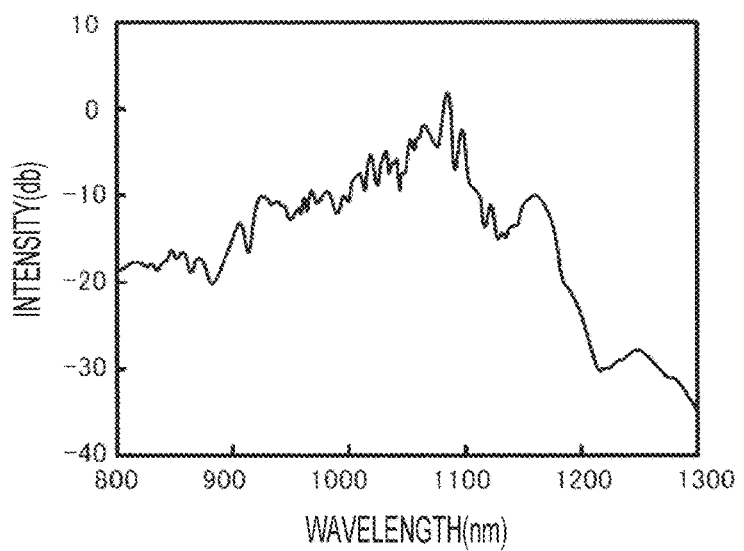
FIG. 15A is a spectrum of SC light.
Figure 15B:
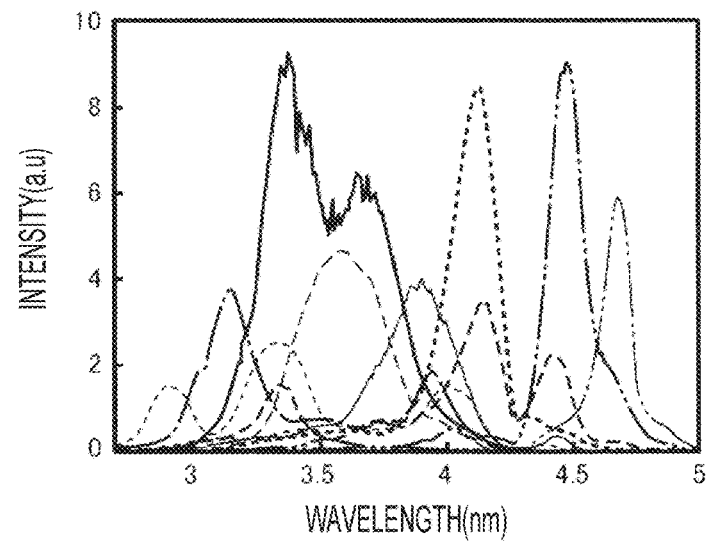
FIG. 15B is a spectrum of mid-infrared light.
Figure 15C:
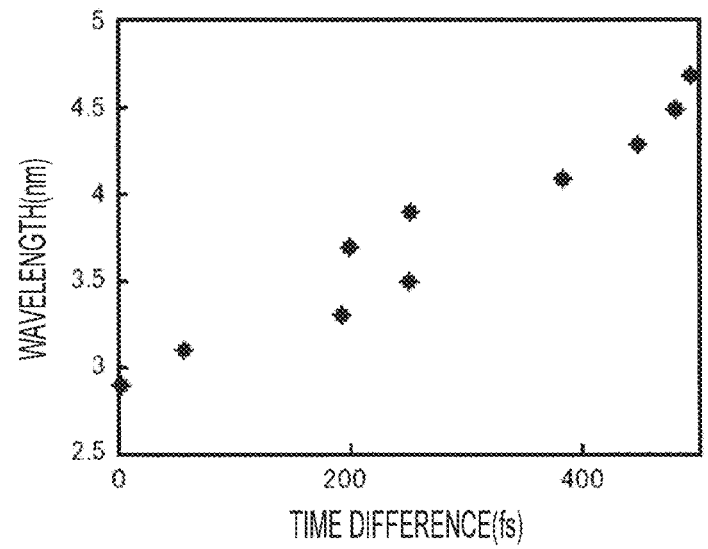
FIG. 15C is a graph illustrating the relation between the time difference and the wavelength of mid-infrared light.

FIGS. 15A to 15C illustrates the experimental results of spectral components focused on a PPMgSLT crystal using a 20 cm all-normal-dispersion-mode photonic crystal fiber (made by NKT photonics), which was a PCF with normal dispersion at 1040 nm. Similar results were observed from experiments with a PPLN crystal in place of the PPMgSLT crystal.

FIG. 15A is a SC spectrum. The optical path difference was adjusted with the delay line. As shown in FIG. 15B, the mid-infrared region was adjusted to 2.9 μm to 4.7 μm. Spectra with different colors are caused by relative time differences. FIG. 15C illustrates the relation between the time difference of the delay line and the spectrum observed by difference frequency generation (DFG). The SC was generated in the normal-dispersion PCF, and thus the central wavelength monotonously increased with the relative time difference. The average output adjusted by this mechanism was of the order of 100 μW. The SC expanded in the PCF for enhancement of the output should have sufficiently high power at a specific wavelength to induce DFG.

(Example 3)

Figure 16A:
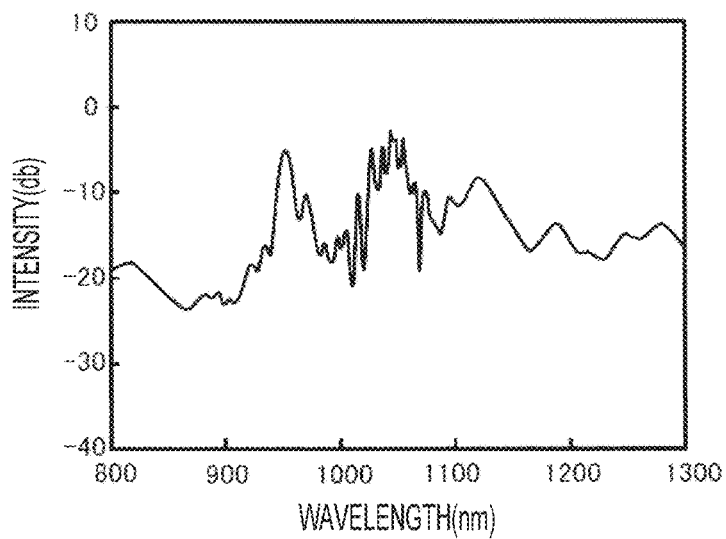
FIG. 16A is a spectrum of Super-continuum (SC) light.
Figure 16B:
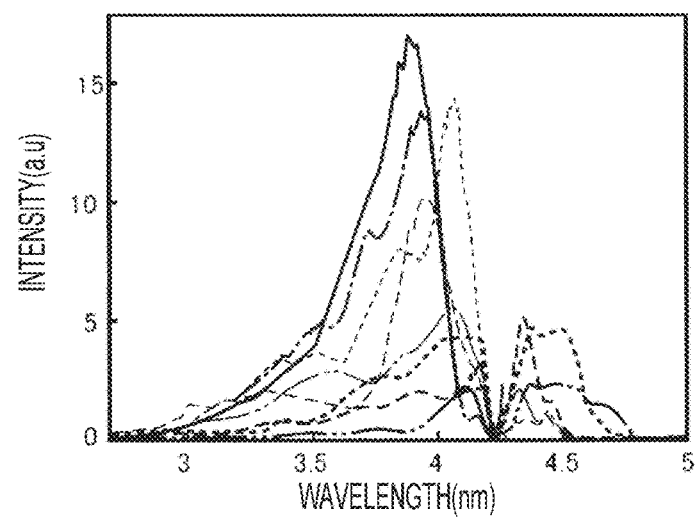
FIG. 16B is a spectrum of mid-infrared light.
Figure 16C:
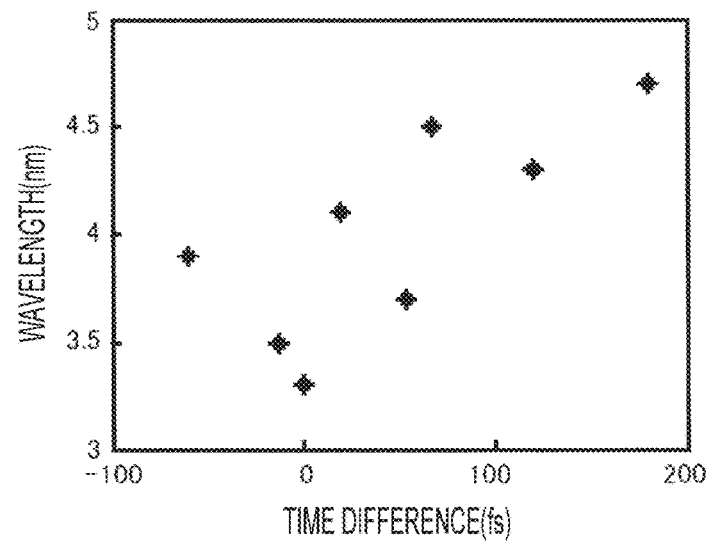
FIG. 16C is a graph illustrating the relation between the time difference and the wavelength of mid-infrared light.

FIGS. 16A to 16C illustrates the experimental results of spectral components focused on a PPMgSLT crystal using a 20 cm photonic crystal fiber (made by NKT photonics), which was a PCF with normal dispersion at 1040 nm. Similar results were observed from experiments with a PPLN crystal in place of the PPMgSLT crystal.

FIG. 16A illustrates a peak at 950 nm that is required for high mid-infrared output. The experimental results show a maximum output of 1.12 mW at a wavelength of 3.9 μm. FIGS. 16B and 16C illustrate the relation between the time difference and the wavelength observed by differential frequency generation (DFG). Since the SC pulses have no linear chirp value, no linear relation is observed between the central wavelength and the time difference. Although the time difference is adjusted over a long range, these spectra are not discriminated from each other. This narrow pulse width, however, generated high-power mid-infrared light.

(Modification 4 of Carbon Isotope Analyzer)

A preferred dehumidification condition is as follows: When the CRDS analytical cell is cooled to −40° C. or less (233K or less), the gas has a low moisture content not causing dewing or freezing at this temperature. In detail, a dehumidifier or a gas drier should preferably be positioned in a carbon dioxide generator (sample inlet unit). Examples of the humidifier include $CaH_2$, $CaSO_4$, $Mg(ClO_4)_2$, molecular sieve, $H_2SO_4$, Sicacide, phosphorus pentoxide, Sicapent (registered trade mark), and silica gel. Among these preferred are phosphorus pentoxide, Sicapent (registered trade mark), $CaH_2$, $Mg(ClO_4)_2$ and molecular sieve. More preferred is Sicapent (registered trade mark). A preferred gas drier is Nafion dryer made by Perma Pure Inc. The humidifier and the gas drier may be used alone or in combination. The "moisture content not causing dewing or freezing at this temperature" was determined through measurement of the dew point. In other words, dehumidification is carried out such that the dew point is −40° C. or less (233K or less). The dew point may be an instantaneous dew point or an average dew point in unit time. The dew point can be measured with a commercially available dew point sensor. Examples of the dew point sensor include a Xentaur (registered trade mark) dew point sensor HTF Al2O3 (available from Mitsubishi Chemical Analytech Co., Ltd.) and Vaisala DRYCAP (registered trade mark) DM70 handy dew point sensor.

It is preferred to minimize the contents of at least carbon, nitrogen, and sulfur elements in the carrier gas used in an organic elemental analyzer. An example of such gas is helium (He). The flow rage of the carrier gas preferably ranges from 50 mL/min to 500 mL/min, more preferably from 100 mL/min to 300 mL/min.

The specifications and dimensions of the carbon isotope analyzer according to the embodiments are as follows:
Detection sensitivity to $^{14}C$: 0.1 dpm/mL,
Capacity of measurement: 400 samples/day, and
Dimensions of the analyzer: 2 m by 1 m by 1 m or less.
The specifications and dimensions of the LSC are as follows:
Detection sensitivity to $^{14}C$: 10 dpm/mL,
Capacity of measurement: 400 samples/day, and
Dimensions of the LSC: 1 m by 1 m by 0.5 m.
The specifications and dimensions of the AMS are as follows:
Detection sensitivity to $^{14}C$: 0.001 dpm/mL,
Capacity of measurement: five samples/day, and
Dimensions of the AMS: 15 m by 10 m by 3 m.
(Pretreatment of Biological Sample)

The pretreatment of the biological sample is categorized into a step of removing carbon sources derived from biological objects and a step of removing or separating the gaseous contaminant in a broad sense. In this embodiment, the step of removing carbon sources derived from biological objects will now be mainly described.

A microdose test analyzes a biological sample, for example, blood, plasma, urine, feces, or bile containing an ultratrace amount of $^{14}C$ labeled compound. Thus, the biological sample should preferably be pretreated to facilitate the analysis. Since the ratio $^{14}C/^{Total}C$ of $^{14}C$ to total carbon in the biological sample is one of the parameters determining the detection sensitivity in the measurement due to characteristics of the CRDS unit, it is preferred to remove the carbon source derived from the biological objects contained in the biological sample.

Provisional Calculation of Ratio $^{14}C/^{Total}C$

Figure 17:
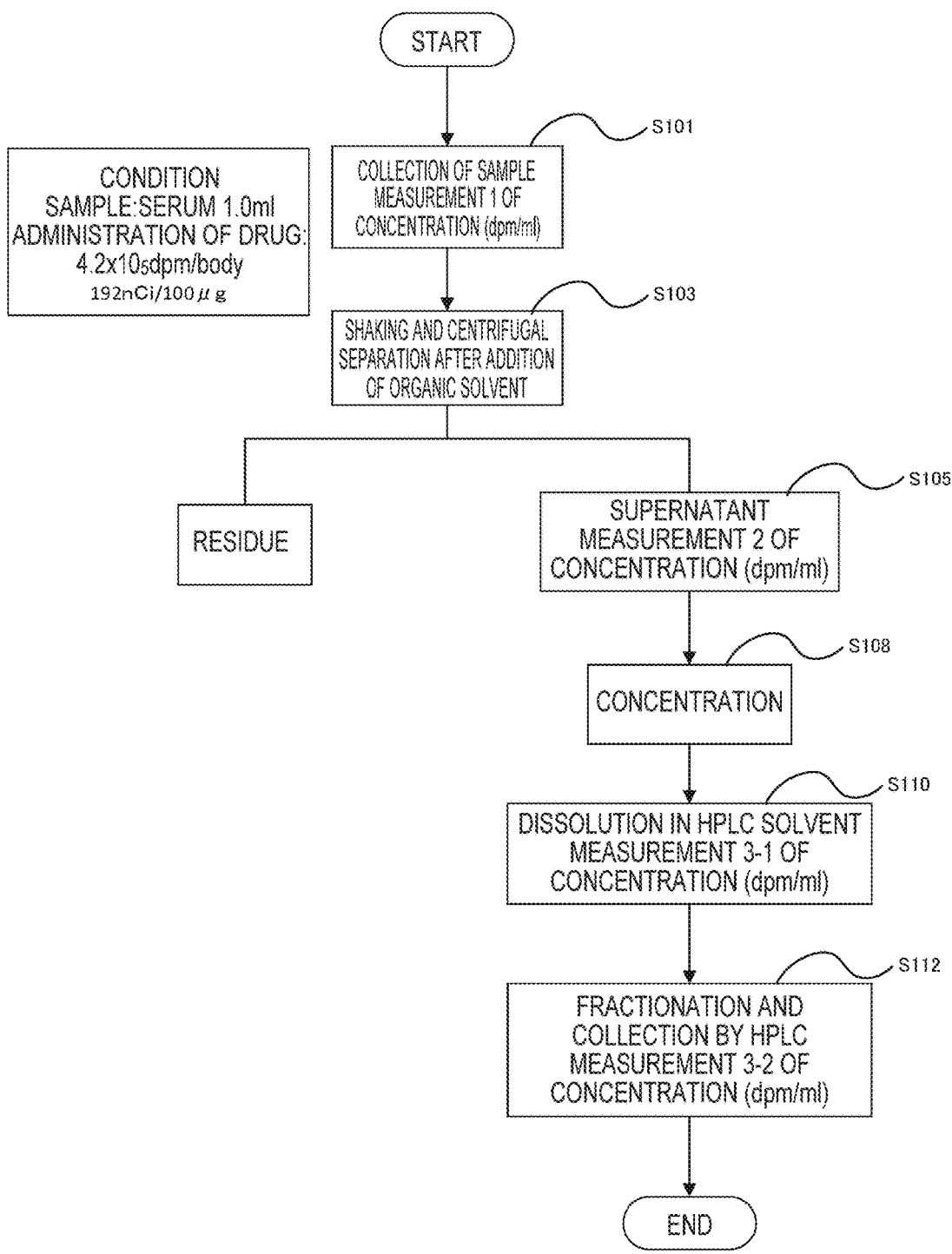
FIG. 17 is a flow chart illustrating the outline of treatment of plasma as a biological sample.

The ratio $^{14}C/^{Total}C$ was calculated with reference to published values (Tozuka et al., "Microdose Study of 14C-Acetaminophen with Accelerator Mass Spectrometry to Examine Pharmacokinetics of Parent Drug and Metabolites in Healthy Subjects" Clinical Pharmacology & Therapeutics 88, 824, 2010). Table 1 summarizes the state, sample, treatment of samples to be measured. FIG. 17 illustrates the flow of the treatment of plasma as a biological sample.

TABLE 1

Treatment available for sample

| | | | Pretreatment for radioactivity determination | | | |
|---|---|---|---|---|---|---|
| State | Sample | Untreated | Preparation of homogenate | Soluene dissolution | Dilution | Treatment with organic solvent |
| Liquid | Plasma | Untreated | — | Done | Done | Done |
| | Urine | Untreated | — | — | Done | Done |
| Solid | Feces | — | Done | Done | Done | Done |
| Liquid | Solution eluted by HPLC | Untreated | — | — | — | — |

In the operation based on the published document, the protein in 1 mL of plasma and 0.5 mL of urine were removed with an organic solvent. The calculated ratio $^{14}C/^{Total}C$ in the sample is in the range of $10^{-11}$ to $^{-14}$ as shown in Table 2. These values suggest that the known pretreatment is insufficient for high detection sensitivity. The values are probably affected by carbon contained in the organic solvent used in the pretreatment and by carbon contained in the organic solvent used as a mobile phase of high-performance liquid chromatography (HPLC).

TABLE 2

Estimated ratio $^{14}C/^{Total}C$ in sample in microdose test

| | Sample (S101) | Supernatant after removal of protein (S105) | HPLC Fractionation 1 (S110) | HPLC Fractionation 2 (S112) |
|---|---|---|---|---|
| Drug (dpm/mL) | 12.78 | 12.53 | 0.017 | 0.194 |
| Total C (mg/mL) | 50.86 | 2964 | $1.55 \times 10^{-1}$ | $2.47 \times 10^{-1}$ |
| $^{14}C/^{Total}C$ | $2.54 \times 10^{-11}$ | $4.27 \times 10^{-13}$ | $5.60 \times 10^{-14}$ | $6.37 \times 10^{-13}$ |

Sample (S101): 50 mgC/mL plasma, supernatant (S105): EtOH 4 mL
Drug: $^{14}C$ level $1.01 \times 10^{-13}$
HPLC Fractionation (S110, S112): calculated under mobile phase A; 10 mmol/L ammonium acetate, mobile phase B; MeOH.

The organic solvent was removed to investigate an improvement in ratio $^{14}C/^{Total}C$.

Organic solvents having high protein removal rates were selected. The study using a solid sample inlet unit indicates that the protein removal rate was about 40% in methanol (MeOH) or about 80% in acetonitrile (MeCN or ACN), which removed the biological carbon source at a high rate. Under assumption of acetonitrile treatment, the ratio $^{14}C/^{Total}C$ after extraction with the organic solvent and drying are shown in Table 3. The improvement is 40 times at maximum. Urine also introduced similar results. In this case, it was estimated that 0.7 to 10 mgC of carbon for 1 mL of human plasma was introduced into the CRDS unit. Since this carbon content complied with the measurable range of the solid sample inlet unit, it was confirmed that 0.1 to 20 mg of carbon was preferably introduced into a gas cell for the CRDS.

These results demonstrate that removal of the carbon source derived from biological objects with organic solvent and removal of the organic solvent are effective pretreatments for measurement of radioactive carbon isotope using the CRDS.

TABLE 3

Carbon content and estimated ratio $^{14}C/C$ after removal of solvent

| | | Supernatant after removal of protein (S105) | HPLC Fractionation 1 (S110) | HPLC Fractionation 2 (S112) |
|---|---|---|---|---|
| ACN After Extraction and drying | Total C (mg C) | 10.17 | $7.47 \times 10^{-1}$ | 1.12 |
| | $^{14}C/^{Total}C$ | $1.24 \times 10^{-10}$ | $2.30 \times 10^{-12}$ | $1.75 \times 10^{-11}$ |

Figure 18:
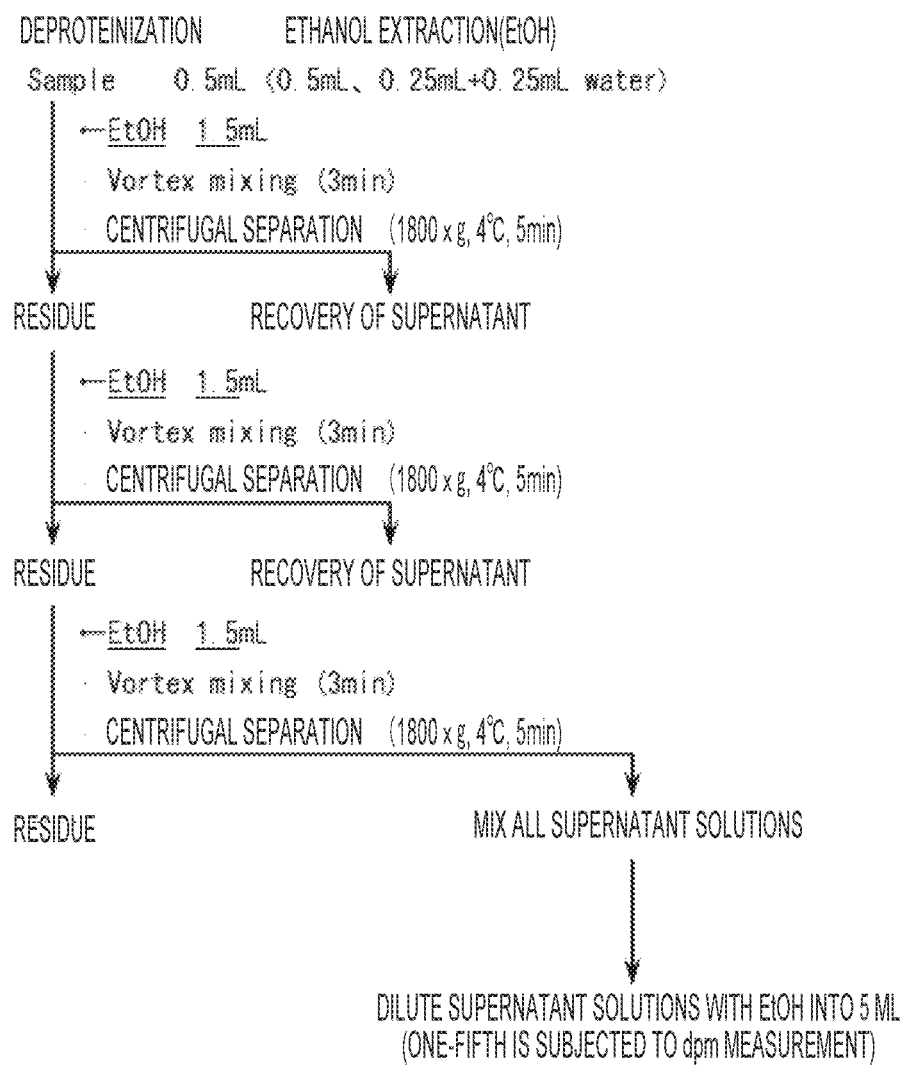
FIG. 18 is a flow chart illustrating the outline of deproteinization treatment of plasma, urine, or feces homogenate as a biological sample.
Figure 19:
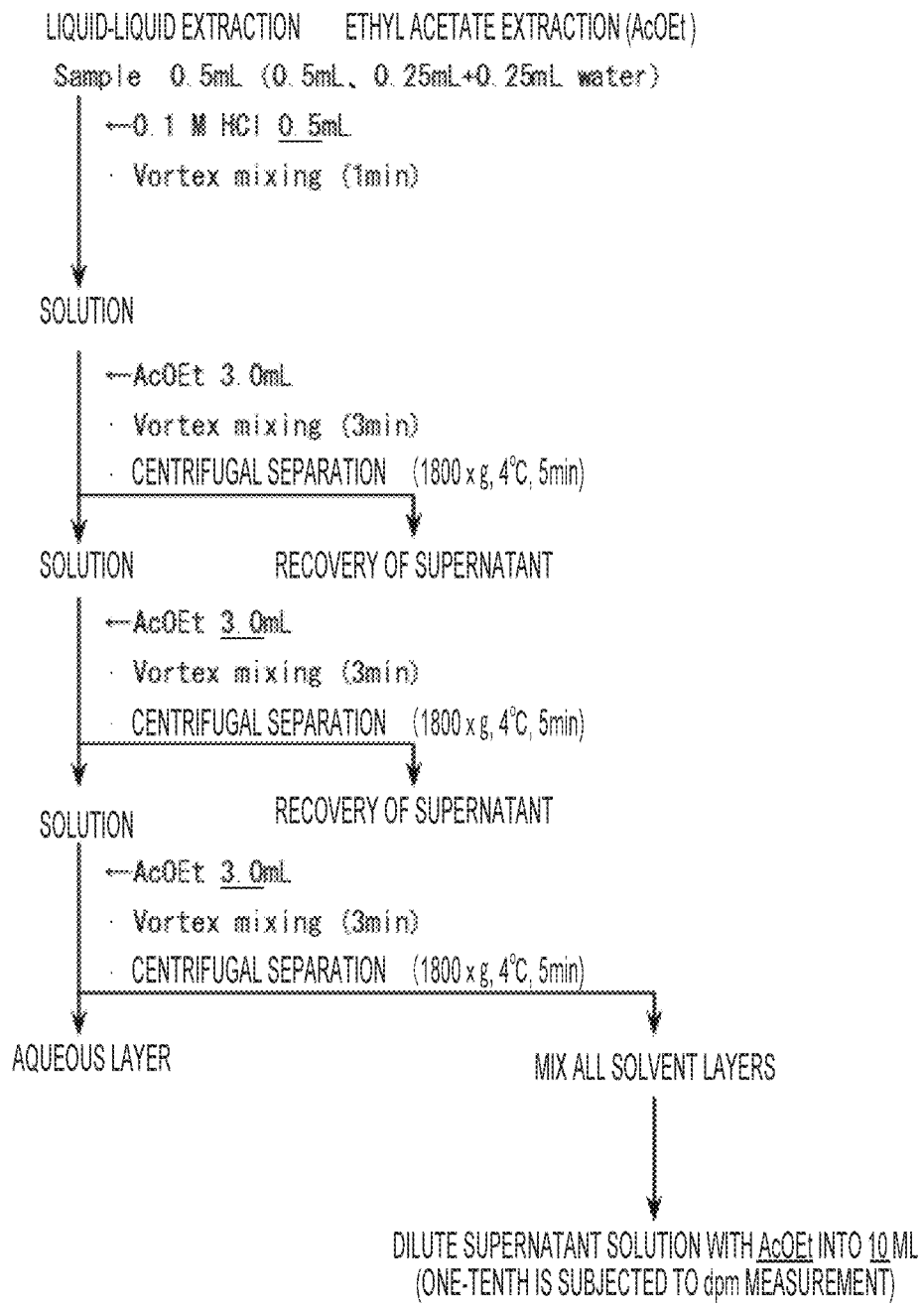
FIG. 19 is a flow chart illustrating the outline of liquid-liquid extraction treatment of plasma, urine, or feces homogenate as a biological sample.
Figure 20:
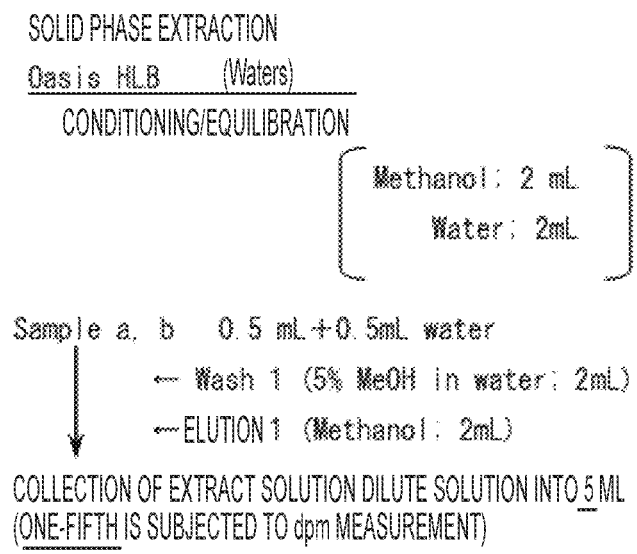
FIG. 20 is a flow chart illustrating the outline of solid-phase extraction treatment of plasma, urine, or feces homogenate as a biological sample.
Figure 21:
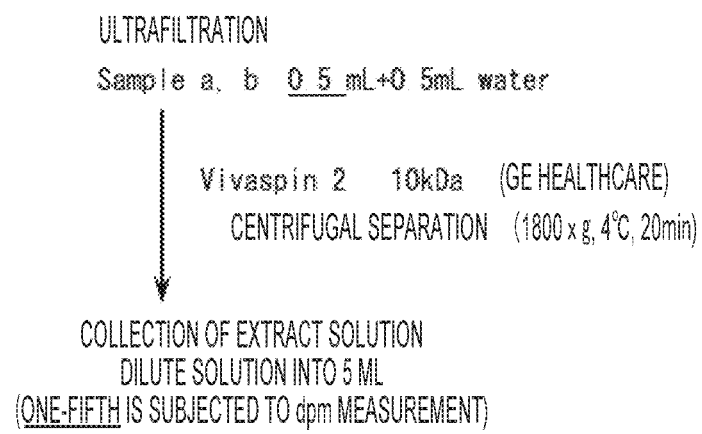
FIG. 21 is a flow chart illustrating the outline of ultrafiltration treatment of plasma, urine, or feces homogenate as a biological sample.
Figure 22:
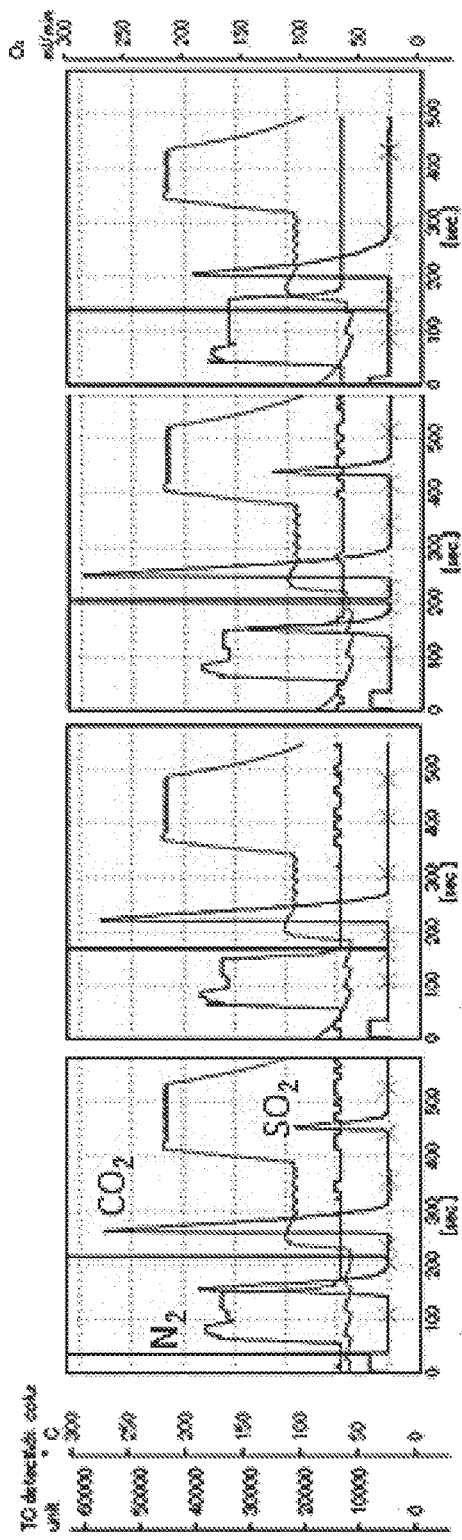
FIG. 22 shows the structural formula, molecular formula, and chromatogram of these samples of Experiment 1.

Pretreatment for reducing carbon intake and for concentrating $^{14}C$ was investigated. The target ratio $^{14}C/^{Total}C$ after $^{14}C$ concentration was set at $10^{-11}$ or more. The step of removing a carbon source derived from biological object and the step of removing the organic solvent (drying) were performed, and the recovery rate of $^{14}C$ and the removal rate of carbon were calculated. Table 4 shows the $^{14}C$ recovery rate and Table 5 shows the removal rate of carbon. Liquid-liquid extraction, solid phase extraction, and ultrafiltration were compared as the step of removing the carbon source derived from biological object. FIG. 18 is a flow chart of the deproteinization; FIG. 19 is a flow chart of the liquid-liquid extraction; FIG. 20 is a flow chart of the solid extraction; and FIG. 21 is a flow chart of the ultrafiltration. The $^{14}C$ source used was $^{14}C$ labeled acetaminophen. The biological samples used were human plasma, human urine, and rat feces 10% homogenate solution. Only the human plasma sample was subjected to ultrafiltration.

The results will now be described. The recovery rate of $^{14}C$ was 91.4% or more in the deproteinization, liquid-liquid extraction, and solid phase extraction. In contrast, the recovery rate of $^{14}C$ from the human plasma sample was 2.6% in the ultrafiltration. The removal rate of carbon was 88.5% or more for all the samples in the solid phase extraction. In contrast, in the deproteinization and the liquid-liquid extraction, the removal rate of carbon was 93.0% or more for the human plasma sample, 79.1% or more for the 10% homogenate solution of the rat feces, 22.8% and 49.5%, respectively, for the human urine sample. These results suggest that some carbon sources derived from a biological matrix can be removed by solid phase extraction but cannot be removed by deproteinization or liquid-liquid extraction in the human urine sample.

These results demonstrate that solid phase extraction is most suitable for human plasma, human urine, and 10% rat faces homogenate solution in the determination of radioactive carbon isotope using the CRDS, and that deproteinization and liquid-liquid extraction are usable for pretreatment of the human plasma and 10% rat feces homogenate solution.

In this Example, since acetaminophen was used as a $^{14}C$ source compound, Oasis HLB (made by Waters) was used as a solid phase. Any solid phase for pretreatment can be used in view of combination with a $^{14}C$ source compound.

The ratio $^{14}C/^{Total}C$ by solid phase extraction was calculated with reference to the published value (Tozuka et al., "Microdose Study of 14C-Acetaminophen with Accelerator Mass Spectrometry to Examine Pharmacokinetics of Parent Drug and Metabolites in Healthy Subjects" Clinical Pharmacology & Therapeutics 88, 824, 2010). The ratio $^{14}C/^{Total}C$ was $10^{-11}$ or more for the human plasma and human urine samples.

TABLE 4

Recovery rate of $^{14}C$ by different treatments

| $^{14}C$ recovery rate | Deproteinization | Liquid-liquid extraction | Solid phase extraction | Ultrafiltration |
|---|---|---|---|---|
| Human plasma | 98.5 | 91.4 | 91.6 | 2.6 |
| Human urine | 94.9 | 100.6 | 93.6 | — |
| Rat feces | 98.9 | 95.1 | 95.1 | — |

TABLE 5

Removal rate of carbon by different treatments

| Carbon removal rate | Deproteinization | Liquid-liquid extraction | Solid phase extraction | Ultrafiltration |
|---|---|---|---|---|
| Human plasma | 93.0 | 97.8 | 98.8 | 84.8 |
| Human urine | 22.8 | 49.5 | 89.7 | — |
| Rat feces | 79.7 | 79.1 | 88.5 | — |

The basic performance of the organic elemental analyzer shown in FIG. 2 was evaluated under the following conditions.

[Procedure]
1. Weighing of Sample

The weight of carbon and the carbon content in the sample was calculated from the following expressions:

Weight of carbon=(weight of sample)×(carbon content in sample)

Carbon content in compound=(molecular weight of carbon in molecular weight of sample)/(molecular weight of sample)

Table 6 shows the samples (compounds) used in the investigation, the molecular formula, the molecular weight, the theoretical carbon content, and purity of the sample.

TABLE 6

| Sample | Formula | Molecular weight | Carbon content (%) | Purity (%) |
|---|---|---|---|---|
| Sulfanilamide | $C_6H_8N_2O_2S$ | 172.2 | 41.8 | 99.7< |
| Glucose | $C_6H_{12}O_6$ | 180.16 | 40.0 | 98< |
| Methionine | $C_5H_{11}NO_2S$ | 149.21 | 40.3 | 99.0< |
| Graphite | C | 12.01 | 100 | 99< |
| Acetaminophen | $C_8H_9NO_2$ | 151.16 | 63.6 | 97< |

2. Setting of Sample and Measurement

The weighed sample was placed into a tin capsule. The capsule was placed on a disk autosampler of an organic elemental analyzer (EA) Vario MICRO cube made by Elementar. The elemental analysis was performed under Condition 1 or 2. In this procedure and the procedure described later, the tin capsule was a tin boat or tin film.
<Condition 1 of Elemental Analysis (CNS Mode)>

Combustion temperature: 1150° C. (instantaneous maximum 1800° C.)
Reduction temperature: 760° C.
Carrier gas: He
Flow rate: 200 mL/min
Oxygen supply: 70 to 80 seconds at 30 mL/min
Oxidation catalyst: cobalt oxide
Reduction catalyst: Reduced copper
Halogen removing catalyst: silver
Humidifier: SICAPENT (made by Merck Millipore)

<Condition 2 of Elemental Analysis (CN Mode)>
Combustion temperature: 950° C. (instantaneous maximum 1800° C.)
Reduction temperature: 600° C.
Carrier gas: He
Flow rate: 200 mL/min
Oxygen supply: 70 to 80 seconds at 30 mL/min
Oxidation catalyst: copper oxide
Reduction catalyst: Reduced copper
Halogen removing catalyst: silver
Humidifier: SICAPENT

[Experiment 1] Combustion of Solid Sample

The sample was combusted (oxidized) in the EA, and the separation and determination from the resulting chromatogram were investigated. The carbon content of each sample was calculated from the area in the chromatograph to determine the combustion rate.

Results 1

Sulfanilamide, glucose, methionine, and graphite were weighed such that the weight of carbon was about 4 mgC, and elemental analysis was performed under Condition 1. Figure shows the structural formula, molecular formula, and chromatogram of these samples.

Elements C, N, and S contained in the sample were converted into oxides during combustion ($NO_x$ was reduced into $N_2$), separated from each other through a heated desorption column, and detected in the form of $CO_2$, $N_2$, and $SO_2$ gas, respectively, with a thermal conductivity detector (TCD). Table 8 shows the carbon content (%) calculated from the peak area in the resulting chromatogram.

TABLE 8

|  | Sulfanilamide | Glucose | L-Methionine | Graphite |
|---|---|---|---|---|
| Weighed (mg) | 10.0 | 10.2 | 10.7 | 4.35 |
| Weight of carbon (mgC) | 4.14 | 4.06 | 4.38 | 4.31 |
| Area | 123025 | 128250 | 128989 | 126452 |
| Carbon content (%) | 41.7 | 39.8 | 40.7 | 98.0 |

The absolute difference between the theoretical carbon content (%) and the observed carbon content (%) was 0.1% for sulfanilamide, 0.2% for glucose, 0.4% for methionine, and 2.0% for fire-retardant graphite. These results demonstrate that 98.0% or more of all the samples including fire-retardant graphite was combusted (oxidized).

[Experiment 2] Evaluation of Effect of Moisture Content and Carbon Dioxide Conversion Rate The effect of moisture on oxidative combustion was investigated.

Preparation of Aqueous Glucose Solution

Glucose (2.5 g) was weighed and was dissolved in pure water into a 5-mL glucose standard solution.

2.5 g×0.4=1.0 gC 1.0 gC/5 mL=0.2 gC/mL        Glc-1 solution

Diluted solutions shown in Table 9 were prepared from the Glc-1 solution.

TABLE 9

| Sample | gC/mL | Diluted solution(mL) | Water(mL) |
|---|---|---|---|
| Glc-1 | 0.2 | — | — |
| Glc-2 | 0.1 | Glc-1 | 0.5 | 0.5 |
| Glc-3 | 0.05 |  | 0.25 | 0.75 |

TABLE 9-continued

| Sample | gC/mL | Diluted solution(mL) | Water(mL) |
|---|---|---|---|
| Glc-4 | 0.04 |  | 0.2 | 0.8 |
| Glc-5 | 0.025 |  | 0.125 | 0.875 |
| Glc-6 | 0.02 |  | 0.1 | 0.9 |
| Glc-7 | 0.01 | Glc-2 |  |  |
| Glc-8 | 0.005 | Glc-3 |  |  |
| Glc-9 | 0.004 | Glc-4 |  |  |
| Glc-10 | 0.0025 | Glc-5 |  |  |
| Glc-11 | 0.002 | Glc-6 |  |  |
| Glc-12 | 0.001 | Glc-7 |  |  |
| Glc-13 | 0.0005 | Glc-8 |  |  |
| Glc-14 | 0.0004 | Glc-9 |  |  |
| Glc-15 | 0.0002 | Glc-11 |  |  |

Figure 23:
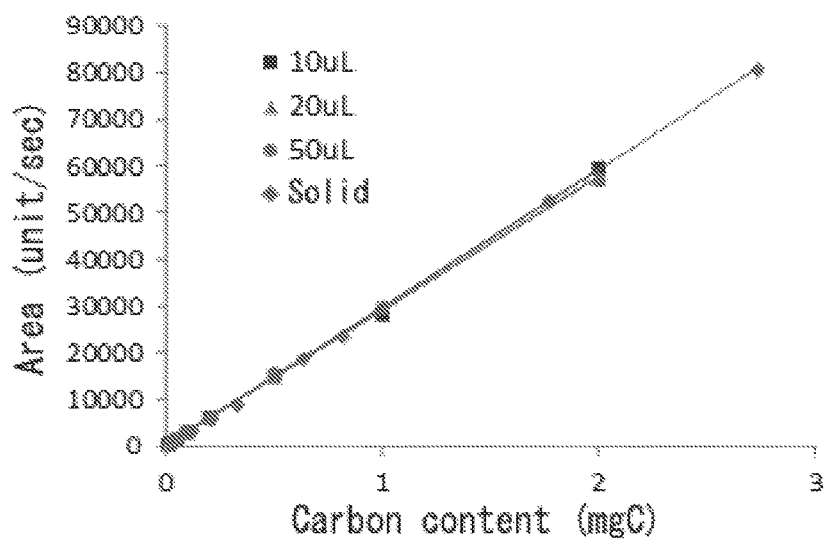
FIG. 23 shows the plot, regression equation, and relative slope of peak area versus carbon content under Condition 1 of Elemental Analysis of Experiment 2.

Aqueous glucose solutions shown in Table 10 were prepared such that the water contents were 10, 20, and 50 μL, respectively, and the carbon contents were in the range of 0.01 to 2.0 mgC, and were each placed in a tin capsule. These samples were measured under Condition 1 of Elemental Analysis. FIG. 23 shows the plot, regression equation, and relative slope of peak area versus carbon content under Condition 1 of Elemental Analysis.

TABLE 10

| Carbon content | Water content (μL) | | |
|---|---|---|---|
| (mgC) | 10 μL | 20 μL | 50 μL |
| 2 | Glc-1 | Glc-2 | Glc-4 |
| 1 | Glc-2 | Glc-3 | Glc-6 |
| 0.5 | Glc-3 | Glc-5 | Glc-7 |
| 0.2 | Glc-6 | Glc-7 | Glc-9 |
| 0.1 | Glc-7 | Glc-8 | Glc-11 |
| 0.05 | Glc-8 | Glc-10 | Glc-12 |
| 0.02 | Glc-11 | Glc-12 | Glc-14 |
| 0.01 | Glc-12 | Glc-13 | Glc-15 |

The combustion rates of the samples were compared from the slopes of the regression equations. The slope of the solid sample glucose was defined as 100%. The relative slope of the sample containing 50 μL of water was 96.1%. This result demonstrates that 95% or more of the sample containing 50 μL of water was combusted. Since the combustion rate equals the conversion rate to carbon dioxide, 90% or more of the conversion rate to carbon dioxide was achieved at a water content within the range of 10 to 50 μL.

[Experiment 3] Evaluation of Dynamic Range

From the results of successful combustion of the sample up to a water content of 50 μL, aqueous glucose solutions were combusted at a water content of 50 μL and a carbon content in the range of 0.05 to 10 mgC, and elemental analysis was carried out under Conditions 1 and 2. A calibration curve was prepared from the resulting area value and the theoretical carbon content of the sample to evaluate the dynamic range for Conditions 1 and 2 of the Elemental Analysis.

<Preparation and Measurement of Sample>

Figure 24:
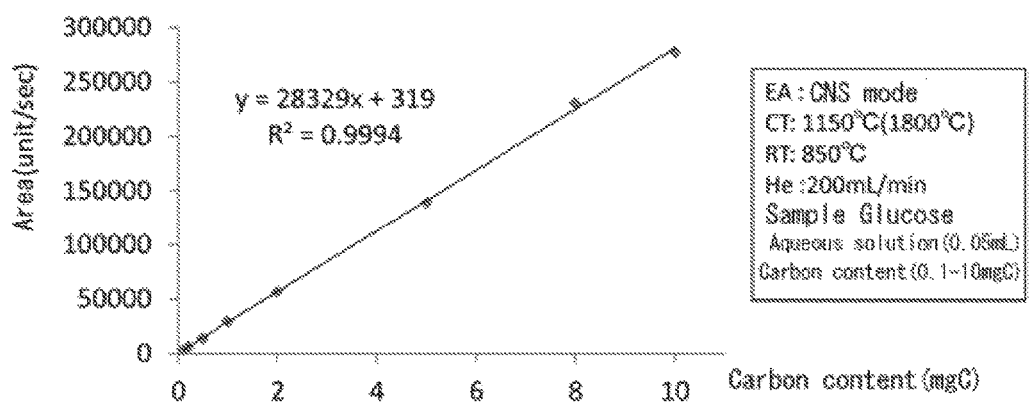
FIG. 24 shows the plot of peak area versus carbon content under Condition 1 of Elemental Analysis of Experiment 3.
Figure 25:
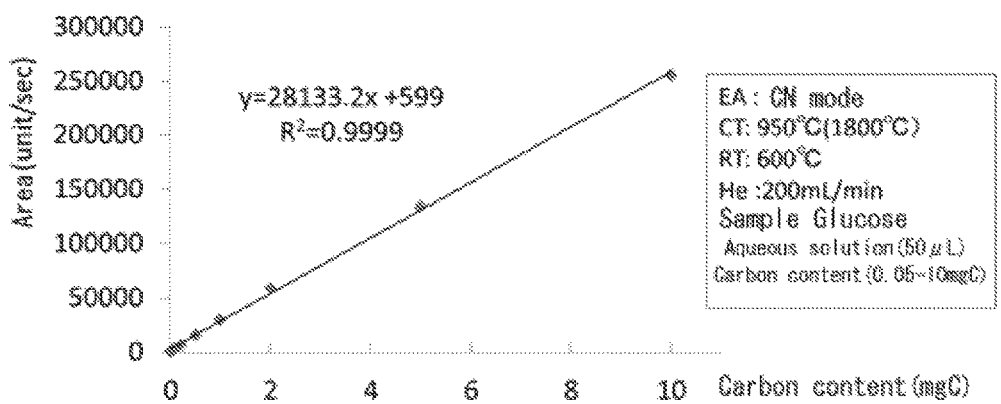
FIG. 25 shows the plot of peak area versus carbon content under Condition 2 of Elemental Analysis of Experiment 3.

Aqueous glucose solutions were prepared such that the carbon contents were within the range of 0.1 to 10 mgC, and subjected to measurement under Conditions 1 and 2 of Elemental Analysis. FIG. 24 shows the plot of peak area versus carbon content under Condition 1 of Elemental Analysis. Table 13 shows the coefficient of variation (CV) and the relative error (RE) under Condition 1 of Elemental Analysis. FIG. 25 shows the plot of peak area versus carbon content under Condition 2 of Elemental Analysis. Table 15 shows the coefficient of variation (CV) and the relative error (RE) under Condition 2 of Elemental Analysis.

TABLE 13

| Carbon content (mgC) | Carbon content (mmol) | Mean area | Standard Dev. | CV (%) | RE (%) |
|---|---|---|---|---|---|
| 0.1 | 0.01 | 3091 | 59.0 | 1.9 | −2.5 |
| 0.2 | 0.02 | 6256 | 84.2 | 1.3 | 5.1 |
| 0.5 | 0.04 | 14170 | 384.7 | 2.7 | −1.6 |
| 1 | 0.08 | 29476 | 140.6 | 0.5 | 3.7 |
| 2 | 0.17 | 56711 | 3394.5 | 6.0 | 0.4 |
| 5 | 0.42 | 138734 | 7781.3 | 5.6 | −1.4 |
| 8 | 0.67 | 230590 | 1341.6 | 0.6 | 2.5 |
| 10 | 0.83 | 277491 | 625.1 | 0.2 | −1.3 |

TABLE 15

| Carbon content (mgC) | Carbon content (mmol) | Mean area | Standard Dev. | CV (%) | RE (%) |
|---|---|---|---|---|---|
| 0.05 | 0.004 | 1965 | 49.8 | 2.5 | −2.9 |
| 0.1 | 0.01 | 3496 | 43.5 | 1.2 | 3.0 |
| 0.2 | 0.02 | 6389 | 120.2 | 1.9 | 2.9 |
| 0.5 | 0.04 | 15380 | 220.0 | 1.4 | 5.1 |
| 1 | 0.08 | 29806 | 721.1 | 2.4 | 3.8 |
| 2 | 0.17 | 58463 | 592.1 | 1.0 | 2.8 |
| 5 | 0.42 | 133748 | 1828.3 | 1.4 | −5.3 |
| 10 | 0.83 | 255550 | 1462.6 | 0.6 | −9.4 |

Within a range of 0.1 to 10 mgC of the weight of the introduced sample in Condition 1 of Elemental Analysis, the coefficient of variation (CV) was 0.2 to 6.0%, relative error (RE) was −2.5 to 5.1%, the coefficient of determination ($R^2$: square of R) was 0.9994, and thus the dynamic range of 100:1. Within a range of 0.05 to 10 mgC of the weight of the introduced sample in Condition 2 of Elemental Analysis, the coefficient of variation (CV) was 0.6 to 2.5%, relative error (RE) was −9.4 to 5.1%, the coefficient of determination ($R^2$: square of R) was 0.9999, and thus the dynamic range of 200:1.

[Experiment 4] Combustion of Biological Sample

Small purpose: Untreated biological samples were subjected to combustion evaluation. In general, introduction of pretreated samples is preferred for achieving high-precision measurement in disposition of drugs. In Experiment 4, however, 10 to 50 μL of plasma and urine samples were combusted so that the effects of biological matrix were also evaluated.

1. Preparation of Sample

Human plasma: a mixture of Caucasian male plasma available from Marshall BioResources Japan Inc. (10 mL×4).

Human urine: Collected from volunteer in the laboratory (men in their twenties to forties, not mixed).

2. Placing Sample in Tin Capsule

Each weighed sample (10 to 50 μL) was placed into a tin capsule.

3. Setting of Sample and Measurement

The encapsulated sample was placed in the elemental analyzer (EA) and analyzed under Condition 2.

Figure 26:
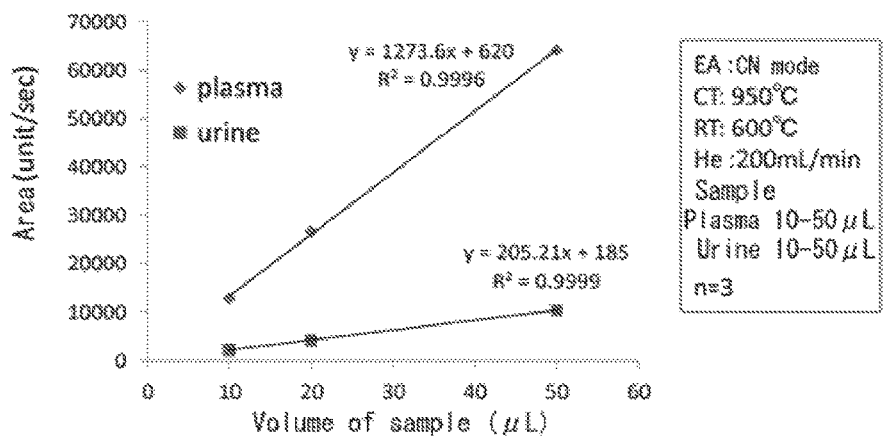
FIG. 26 shows the plot of peak area versus volume of sample (result 4) of Experiment 4.
Figure 27:
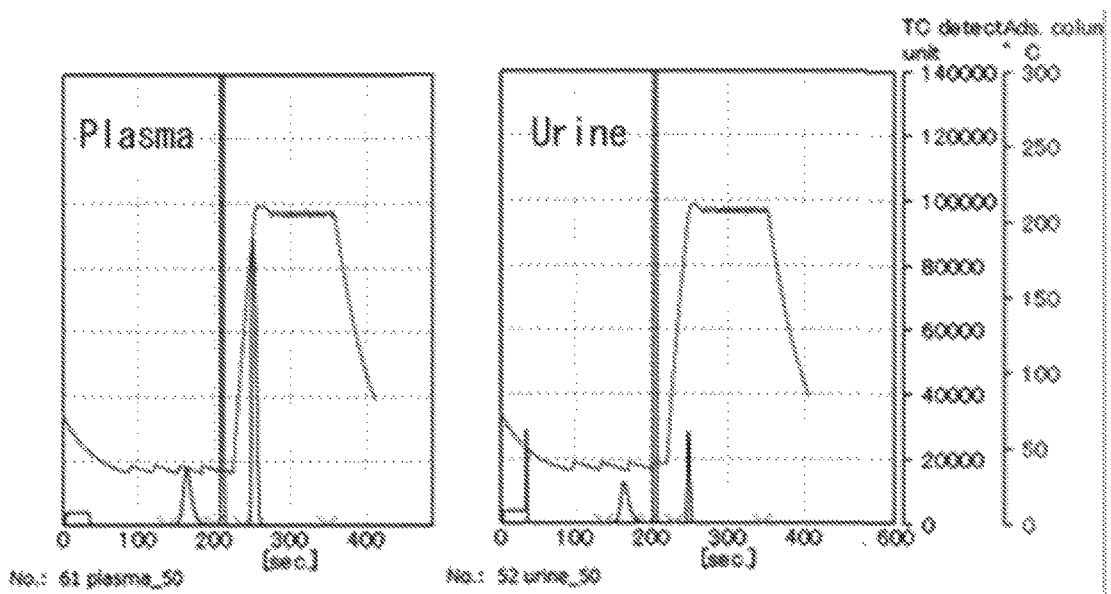
FIG. 27 shows the resulting chromatograms of Experiment 4.

FIG. 26 shows the plot of peak area versus volume of sample (result 4). FIG. 27 shows the resulting chromatograms.

The coefficient of determination was 0.9996 or more in both the plasma and the urine, indicating high linearity corresponding to the volume of the sample. Chromatograms were satisfactory, indicating that untreated biological samples were successfully combusted. Table 18 shows the carbon content in the biological samples calculated from the results of 50 μL of introduced volume.

TABLE 18

| | Carbon content (mgC/mL) |
|---|---|
| Plasma | 47.5 |
| Urine | 7.74 |

The combustion tests of the samples in the EA demonstrate that solid samples and aqueous solution samples containing 50 μL of water can be successfully combusted. When the slope of the calibration curve of the solid sample is defined as a conversion rate to carbon dioxide of 100%, the slope of calibration curve of the sample containing 50 μL of water, which is the most flame resisting sample, was 96.1%. In this case, the dynamic range is probably 100:1 or better. These results demonstrate that the EA is applicable to a sample inlet of the CRDS device.

[Experiment 5]

The recovery and determination of $^{14}CO_2$ generated by combustion of $^{14}C$ sample confirmed that the conversion rate to carbon dioxide in the sample inlet was 90% or more. The $^{14}C$ labeled compound used was acetaminophen. Table 19 shows the results (Result 5) of Experiment 5.

TABLE 19

| Result 5 | | |
|---|---|---|
| Sample | Carbon content (mgC) | $^{14}C$ Recovery rate (%) |
| Sample1-1 | 4.1 | 99.95 |
| Sample1-2 | 9.1 | 99.26 |
| Sample1-3 | 14.1 | 96.90 |

The recovery rate was measured at a constant $^{14}C$ content and variable total C contents. Even at a C content of 14.1 mgC, the conversion rate of $^{14}C$ was 90% or more. The results demonstrate that a substantial amount of $^{14}C$ in the compound was converted to $^{14}CO_2$, the recovery rate of $^{14}C$ was 90% or more based on the conversion rate to carbon dioxide.

A pretreatment in the AMS, which is a typical known measurement of radioactive carbon isotope prior to the present invention, is compared with the pretreatment based on the principle shown in FIG. 2 in the carbon dioxide isotope generator 40 of the present invention.

The pretreatment in the AMS involves a preparative step of washing and dilution of a biological sample of interest, a conversion step of converting the biological sample to carbon dioxide, a reduction step, and a press step. To test 100 samples, AMS requires two operators and at least 6 to 7 days. The cost for measurement is 4 million yen (approximately, 40 thousand dollars), i.e., 40 thousand yen per sample, refer to document published by Accelerator Analysis Center).

In contrast, the pretreatment by CRDS of the invention involves a step of removing biologically removed carbon from a biological sample; a step of converting the treated biological sample into carbon dioxide; a step of purification (concentration and removal of gaseous contaminant); and a step of dehumidification and cooling. In the case of measurement of 100 samples, the step of converting the biological sample into the carbon dioxide biological sample and the succeeding steps can be automated; hence, these samples can be measured by an operator within a day or two days. The estimated cost is ten thousand yen or less (one hundred to thousand yen per sample).

An apparatus of the AMS requires a dedicated building with an area about half a tennis court, while a device of the CRDS has a reduced installation area corresponding to the desktop with increased flexibility of arrangement.

Pretreatments for LSC and AMS, which are typical established measurement methods of radioactive carbon isotope prior to the present invention are compared with the pretreatment based on the principle shown in FIG. 2 in the carbon dioxide isotope generator 40 of the present invention.

The pretreatment prior to the measurement of the biological sample by the LSC requires several minutes to about 28 hours depending on the type of the biological sample. The pretreatments of urine and blood are exemplified as follows:

Before the urine sample is subjected to LSC measurement, the urine sample may be diluted with distilled water if necessary. Such a pretreatment requires several minutes.

The LSC involves detection of fluorescence from a scintillator receiving radiation rays from the sample and thus determination of the radiation dose. In the LSC measurement of blood, a pigment derived from the blood may interfere with the fluorescent light and thus hinder the accurate determination. In such a case, a tissue solubilizer Soluene-350 (Perkin Elmer) is added to a blood sample, the system is heated at 40° C. to 60° C. for several hours, and hydrogen peroxide (30%) is added to decolorize the blood pigment, in some cases. This pretreatment process requires about 4 to 24 hours. An alternative pretreatment involves drying a blood sample, oxidative combustion of carbon in the sample and trapping of the resulting carbon dioxide with, for example, amine.

This pretreatment requires about 4 to 24 hours.

The pretreatment process for AMS analysis of a biological sample involves steps one to five as schematically described below. Examples of the biological sample include blood, plasma, urine, feces, and bile.

The first step involves optional dilution of a biological sample with a diluent, and fractionation of the diluted sample. The preferred diluent is, for example, ultrapure water or a blank sample.

The second step involves oxidation of the fractionated sample to convert carbon contained in the sample into carbon dioxide.

The third step involves isolation and purification of carbon dioxide from, for example, water or nitrogen. The carbon content of the purified carbon dioxide is determined.

The fourth step involves the reduction of the purified carbon dioxide into graphite. For example, carbon dioxide is mixed with iron powder and hydrogen gas (i.e., reductants), and the mixture is heated in an electric furnace for reducing carbon dioxide into graphite.

The fifth step involves compression of the resultant graphite.

This pretreatment process requires about six days.

The pretreatment process for LSC requires several minutes to about 28 hours and the pretreatment process for AMS requires about six days. In contrast, the step of generating carbon dioxide based on the principle shown in FIG. 2 according to this embodiment requires several minutes to about 28 hours. Examples of the pretreatment process involve dilution, extraction, and concentration. In principle, the pretreatment process is performed until the conversion of carbon contained in an analyte into carbon dioxide through complete combustion of the carbon. According to the present embodiment, the pretreatment time can be reduced to several minutes to about 1.5 hours per analyte. For example, this process does not need the tissue solubilization step and the decolorization step, which are essential for LSC measurement of a blood sample. The pretreatment process shown in FIGS. 18 to 21 accordingly requires several minutes to about 1.5 hours per analyte.

(Analysis of Carbon Isotope)

The analysis of radioactive isotope $^{14}C$ as an example of the analyte will now be described.

(A) Carbon isotope analyzer 1 shown in FIG. 1 is provided. Biological samples, such as blood, plasma, urine, feces, and bile, containing $^{14}C$ are also prepared as radioactive isotope $^{14}C$ sources.

(B) The biological sample is pretreated to remove protein and thus to remove the biological carbon source. Examples of deproteinization include insolubilization of protein with acid or organic solvent; ultrafiltration and dialysis based on a difference in molecular size; and solid-phase extraction. As described below, deproteinization with organic solvent is preferred, which can extract the $^{14}C$ labeled compound and the organic solvent can be readily removed after treatment.

The deproteinization with organic solvent involves addition of the organic solvent to a biological sample to insolubilize protein. The $^{14}C$ labelled compound adsorbed on the protein is extracted to the organic solvent in this process. To enhance the recovery rate of the $^{14}C$ labeled compound, the solution is transferred to another vessel and fresh organic solvent is added to the residue to further extract the labeled compound. The extraction operations may be repeated several times. In the case that the biological sample is feces or an organ such as lung, which cannot be homogeneously dispersed in organic solvent, the biological sample should preferably be homogenized. The insolubilized protein may be removed by centrifugal filtration or filter filtration, if necessary.

The organic solvent is then removed by evaporation to yield a dry $^{14}C$ labeled compound. The carbon source derived from the organic solvent can thereby be removed. Preferred examples of the organic solvent include methanol (MeOH), ethanol (EtOH), and acetonitrile (ACN). Particularly preferred is acetonitrile.

(C) The pretreated biological sample was combusted to generate gas containing carbon dioxide isotope $^{14}CO_2$ from the radioactive isotope $^{14}C$ source. $N_2O$ and CO are then removed from the resulting gas. In a preferred embodiment, $^{14}CO_2$ is removed with a device shown in FIG. 2 or 3.

(D) Preferably, moisture is removed from the resultant $^{14}CO_2$ gas. For example, moisture is preferably removed from the $^{14}CO_2$ gas in the carbon dioxide isotope generator 40 by allowing the $^{14}CO_2$ gas to pass through a desiccant (e.g., calcium carbonate) or cooling the $^{14}CO_2$ gas for moisture condensation. Formation of ice or frost on the optical resonator 11, which is caused by moisture contained in the $^{14}CO_2$ gas, may lead to a reduction in reflectance of the mirrors, resulting in low detection sensitivity. Thus, removal of moisture improves analytical accuracy. The $^{14}CO_2$ gas is preferably cooled and then introduced into the spectrometer 10 for the subsequent spectroscopic process. Introduction of the $^{14}CO_2$ gas at room temperature significantly varies the temperature of the optical resonator, resulting in a reduction in analytical accuracy.

(E) The $^{14}CO_2$ gas is fed into the optical resonator 11 having the pair of mirrors 12a and 12b. The $^{14}CO_2$ gas is preferably cooled to 273K (0° C.) or less to enhance the absorption intensity of excitation light. The optical resonator 11 is preferably maintained under vacuum because a reduced effect of the external temperature on the optical resonator improves analytical accuracy.

(F) Primary light (optical frequency comb) is generated from the single light source 23. The first light is transmitted through the first optical fiber 21. The first light is also transmitted through the second optical fiber 22 for wavelength conversion splitting from the first optical fiber 21, to generate secondary light having a wavelength different from that of the first light. The second light is combined with the first light downstream of the first optical fiber 21, and the first light and the second light are transmitted through the non-linear optical crystal 25, to generate excitation light of 4.5 µm, which is the absorption wavelength of the carbon dioxide isotope $^{14}CO_2$.

(G) The carbon dioxide isotope $^{14}CO_2$ is in resonance with the light. To improve analytical accuracy, the external vibration of the optical resonator 11 is preferably reduced by a vibration absorber to prevent a perturbation in distance between the mirrors 12a and 12b. During resonance, the downstream end of the first optical fiber 21 should preferably abut on the mirror 12a to prevent the light from coming into contact with air. The intensity of light transmitted from the optical resonator 11 is then determined. As illustrated in FIG. 5, the transmitted light may be dispersed into spectral components, and the intensities of the spectral components may be determined.

(H) The concentration of carbon isotope $^{14}C$ is calculated from the intensity of the transmitted light.

(Other Embodiments)

Although the embodiment of the present invention has been described above, the descriptions and drawings as part of this disclosure should not be construed to limit the present invention. This disclosure will enable those skilled in the art to find various alternative embodiments, examples, and operational techniques.

The carbon isotope analyzer according to the embodiment has been described by focusing on the case where the analyte is radioisotope $^{14}C$. The carbon isotope analyzer can analyze stable isotopes $^{12}C$ and $^{13}C$ besides radioisotope $^{14}C$. In such a case, excitation light of 2 µm or 1.6 µm is preferably used in, for example, absorption line analysis of $^{12}CO_2$ or $^{13}CO_2$ based on analysis of $^{12}C$ or $^{13}C$.

In the case of absorption line analysis of $^{12}CO_2$ or $^{13}CO_2$, the distance between the mirrors is preferably 10 to 60 cm, and the curvature radius of the mirrors is preferably equal to or longer than the distance therebetween.

Although the carbon isotopes $^{12}C$, $^{13}C$, and $^{14}C$ exhibit the same chemical behaviors, the natural abundance of $^{14}C$ (radioisotope) is lower than that of $^{12}C$ or $^{13}C$ (stable isotope). Artificial enrichment of the radioisotope $^{14}C$ and accurate analysis of the isotope can be applied to observation of a variety of reaction mechanisms.

The carbon isotope analyzer according to the embodiment may further be provided with a third optical fiber composed of a non-linear fiber that splits from the first optical fiber and is coupled with the first optical fiber downstream of the splitting point. Combination of the first to third optical fibers can generate light of two or more different frequencies.

A medical diagnostic device or environmental measuring device including the configuration described above in the embodiment can be produced as in the carbon isotope analyzer. The light generator described in the embodiments can also be used as a measuring device.

As described above, the present invention certainly includes, for example, various embodiments not described herein. Thus, the technological range of the present invention is defined by only claimed elements of the present invention in accordance with the proper claims through the above descriptions.

REFERENCE SIGNS LIST 1 carbon isotope analyzer
10 spectrometer
11 optical resonator
12 mirror
13 piezoelectric element
14 diffraction grating
15 photodetector
16 cell
18 vacuum device
19 Peltier device
20 light generator
21 first optical fiber
22 second optical fiber
23 light source
25 non-linear optical crystal
26 optical switch
28 delay line
30 arithmetic device
40 carbon dioxide isotope generator

The invention claimed is:

1. A carbon isotope analyzer comprising:
a carbon dioxide isotope generator comprising a combustion unit that generates gas containing carbon dioxide isotope from carbon isotope; and a carbon dioxide isotope purifying unit, wherein the carbon dioxide isotope purifying unit comprises a dehumidifier;
a spectrometer comprising an optical resonator having a pair of mirrors and a cooler that cools the optical resonator, and a photodetector that determines the intensity of light transmitted from the optical resonator; and
a light generator comprising a light source; a first optical fiber to transmit a light beam from the light source; a second optical fiber for wavelength conversion, the second optical fiber splitting from the first optical fiber at a splitting node and coupling with the first optical fiber at a coupling node downstream of the splitting node; and a non-linear optical crystal that generates light having an absorption wavelength of the carbon dioxide isotope based on the difference in frequency between light beams transmitted through the optical crystal.

2. The carbon isotope analyzer of claim 1, wherein the dioxide isotope purifying unit comprises at least one of a gaseous contaminant separator and a carbon dioxide isotope enricher.

3. The carbon isotope analyzer according to claim 1, wherein the carbon isotope is radioactive carbon $^{14}C$, and the carbon dioxide isotope is radioactive carbon dioxide $^{14}CO_2$.

4. The carbon isotope analyzer of claim 1, wherein the light source generates frequency comb light.

5. The light source of claim 1, the light source comprises a fiber laser.

6. The carbon isotope analyzer of claim 1, wherein the light having an absorption wavelength of the carbon dioxide isotope is light of a 4.5-µm wavelength range.

7. The carbon isotope analyzer of claim 1, wherein carbon dioxide isotope generator comprises a total organic carbon gas generator that generates the carbon dioxide isotope.

8. The carbon isotope analyzer of claim 1, wherein the first optical fiber extends from the light source to the optical resonator.

9. The carbon isotope analyzer of claim 1, wherein the first optical fiber comprises a fiber component (a) extending from the light source to the non-linear optical crystal; and a fiber component (b) for a mid-infrared extending from the non-linear optical crystal to the optical resonator.

10. The carbon isotope analyzer of claim 1, the light generator further comprises an optical transmitter that transmits light from the non-linear optical crystal to the optical resonator.

11. The carbon isotope analyzer of claim 10, wherein the first optical fiber is the fiber component (a) extending from the light source to the non-linear optical crystal.

12. The carbon isotope analyzer of claim 1, wherein the light generator further comprises:
- an optical lens between a coupling node between the first and second optical fibers and the non-linear optical crystal; and/or
- another optical lens between the non-linear optical crystal and the optical resonator.

13. The carbon isotope analyzer of claim 1, wherein the first optical fiber has a downstream end abutting on one of the mirrors.

14. The carbon isotope analyzer of claim 1, wherein the second optical fiber comprises a nonlinear optical fiber.

15. The carbon isotope analyzer of claim 1, wherein the spectrometer further comprises a vacuum device that accommodates the optical resonator.

16. The carbon isotope analyzer of claim 1, wherein the spectrometer further comprises a vibration dampener.

17. The carbon isotope analyzer of claim 1, wherein the spectrometer further comprises a diffraction grating that disperses the transmitted light, and the photodetector comprises a first sub-detector (a) and a second sub-detector (b) that detect transmitted light beams having different wavelengths.

18. The carbon isotope analyzer of claim 1, wherein the non-linear optical crystal is selected from a PPMGSLT crystal, PPLN crystal, and GaSe crystal.

19. The carbon isotope analyzer of claim 1, wherein the analyzer has a detection sensitivity of about 0.1 dpm/ml to a radioactive carbon isotope $^{14}C$.

* * * * *